United States Patent [19]

Chu

[11] Patent Number: 5,215,883

[45] Date of Patent: Jun. 1, 1993

[54] ELECTROPHORETIC MOBILITY OF FLUOROPHORE LABELED PARTICLES IN GELS BY FLUOROPHORE MOVEMENT AFTER PHOTOBLEACHING

[75] Inventor: Benjamin Chu, Setauket, N.Y.

[73] Assignee: The Research Foundation, Albany, N.Y.

[21] Appl. No.: 550,713

[22] Filed: Jul. 9, 1990

[51] Int. Cl.$^5$ .................. G12Q 1/68; C12M 1/00; G01N 21/00

[52] U.S. Cl. .................. 435/6; 435/287; 422/82.08; 356/344; 935/85; 935/77; 204/299 R; 204/180.1; 204/182.8

[58] Field of Search ........... 204/299 R, 180.1, 182.8; 356/344; 435/6, 287, 291, 808; 935/85-87, 111, 77, 76; 422/68.1, 82.08

[56] References Cited

U.S. PATENT DOCUMENTS 4,222,744 9/1980 McConnell .................. 436/514
4,675,095 6/1987 Kambara et al. .................. 204/299 R
4,832,815 5/1989 Kambara et al. .................. 204/299 R

OTHER PUBLICATIONS

Chu et al., Biopolymers, 28, 1491–1494 (1989).
Wang et al., Physical Review Letters, 63 (22), 2528–2531 (1989).
Wu et al., Biopolymers, 29, 491–500 (1990).
Schwartz et al., Cell, 37, 67–75 (1984).
Carle et al., Science, 232, 65–68 (1986).
Cantor et al., Ann. Rev. Biophys. Chem., 17, 287–304 (1988).
Anand, Trends Genet., 2, 278–283 (1986).
Chu et al., Biopolymers, 27, 2005–2009 (1988).
Lerman et al., Biopolymers, 21, 995–997 (1982).
Lumpkin, et al., Biopolymers, 21, 2315–2316 (1982).
Lumpkin et al., Biopolymers, 24, 1573–1593 (1985).
Slater et al., Physical Review Letters, 55 (15) 1579–1582.
Slater et al., Biopolymers, 25, 431–454 (1986).
Noolandi et al., Phys. Rev. Lett., 58 (23), 2428–2431 (1987).
Hervet et al., Biopolymers, 26, 727–742 (1987).
Zimm, Phys. Rev. Lett., 61 (26), 2965–2968 (1988).
Noolandi et al., Science, 243, 1456–1458 (1989).
Deutsch, Science, 240, 922–924 (1988).
Deutsch, J. Chem. Phys., 90 (12), 7436–7441 (1989).
Deutsch et al., J. Chem. Phys., 90 (4), 2476–2485 (1989).
Holtzwarth et al., Nucleic Acids Res., 15, 10031–10044 (1987).
Smith et al., Science, 243, 203–206 (1989).
Schwartz et al., Letters to Nature, 338, 520–522 (1989).
Holtzwarth et al., Biopolymers, 28, 1043–1058 (1989).
Smith et al., Proc. Natl. Acad. Sci. USA, 75, 2759–2763 (1978).

(List continued on next page.)

Primary Examiner—James C. Housel
Assistant Examiner—William K. Y. Chan

[57] ABSTRACT

A process and apparatus for detecting the mobility of fluorescently labeled molecules in response to a force is disclosed. The fluorescently labeled molecules are placed in a fluid medium such as an electrophoretic gel in a capillary tube. An electric field is applied to induce the movement of the molecules. A region of the labeled molecules is photobleached leaving a geometrically defined region which has not been photobleached. The region which has not been photobleached is excited by a reading beam. The reading and the photobleaching beams can be generated by focusing a laser through a diffraction grading. The intensity produced by the interaction of the reading beam in the geometrically defined region of the molecule is detected by a photo detector. In detecting more than one species of labeled molecules, the reading beam which has a second geometrically defined configuration is modulated as a function of the velocity of the labeled molecules through the fluid medium. The frequency of the resulting intensity pattern produced by the interaction of the modulated, oscillating reading beam and the movement of the labeled molecules through the fluid medium are analyzed.

22 Claims, 19 Drawing Sheets

OTHER PUBLICATIONS

Lanni & Ware, *Rev. Sci. Instrum.*, 53 (6), 905–908 (1982).
Wahl, *Biophys. Chem.*, 22, 317–321 (1985).
Peters et al., *Biochim. Biophys. Acta*, 367 282–294 (1974).
Axelrod et al., *Biophys. J.*, 16, 1055–1069 (1976).
Jacobson et al., *Biochim. Biophys. Acta*, 433, 215–222 (1976).
Koppel et al., *Biophys. J.*, 16, 1315–1329 (1976).
Lanni et al., *Biophys. J.*, 35, 351–364 (1981).
Kasper et al., *J. Chromatogr.*, 458, 303–312 (1988).
Rhee et al., *J. Phys. Chem.*, 88, 3944–3946 (1984).
Kim et al., *J. Phys. Chem.*, 88, 3946–3949 (1984).
Fangman, *Nucleic Acids Res.*, 5 (3), 653–665 (1978).
Slater et al., *Biopolymers*, 27, 509–524 (1988).
Righetti et al., *Journal of Biochemical & Biophysical Methods*, 4, 347–363 (1981).
Stellwagen, *Biopolymers*, 24, 2243–2255 (1985).
Serwer et al., *Electrophoresis*, 4, 273–276 (1983).
Serwer et al., *Analytical Biochemistry*, 158, 72–78 (1986).

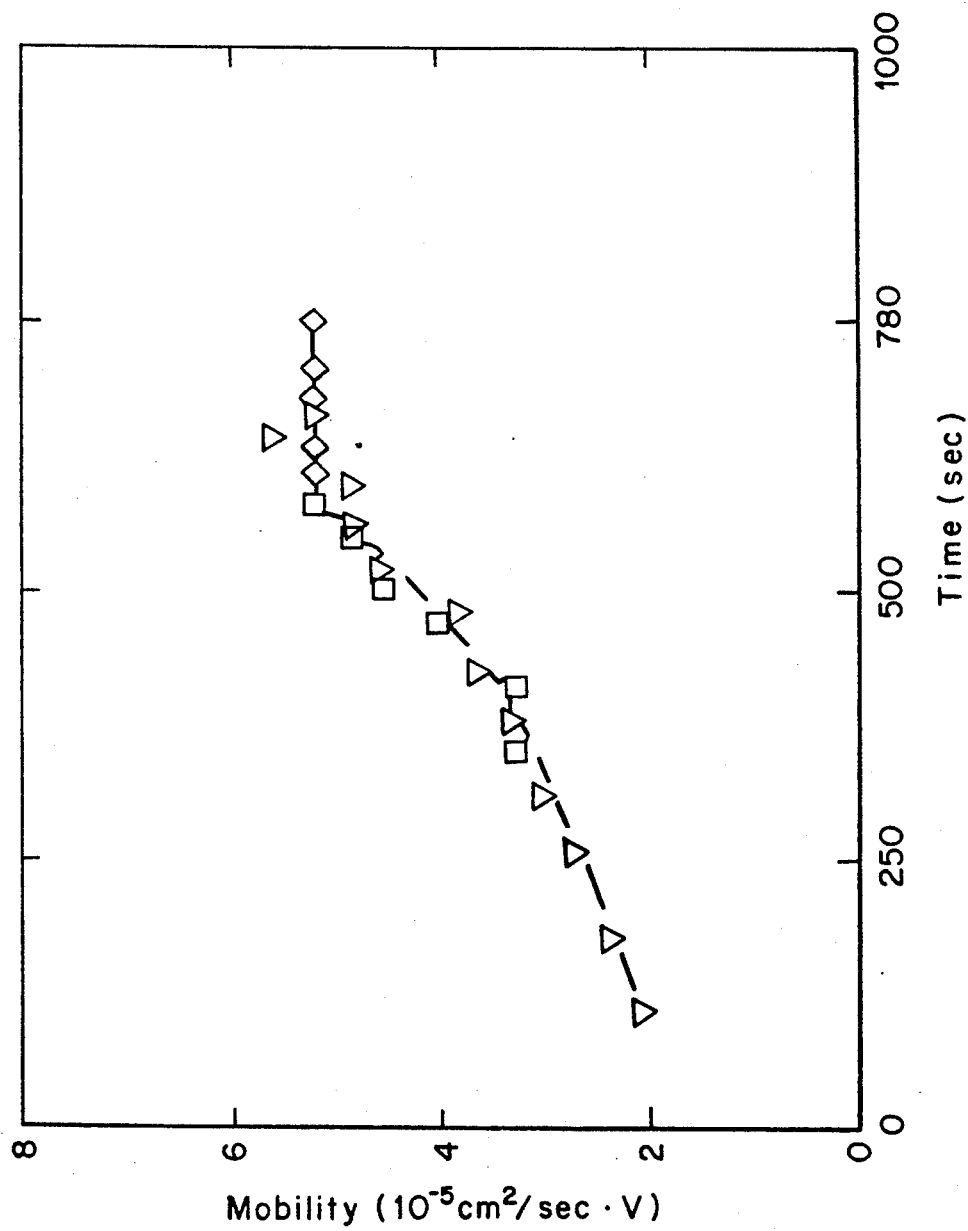

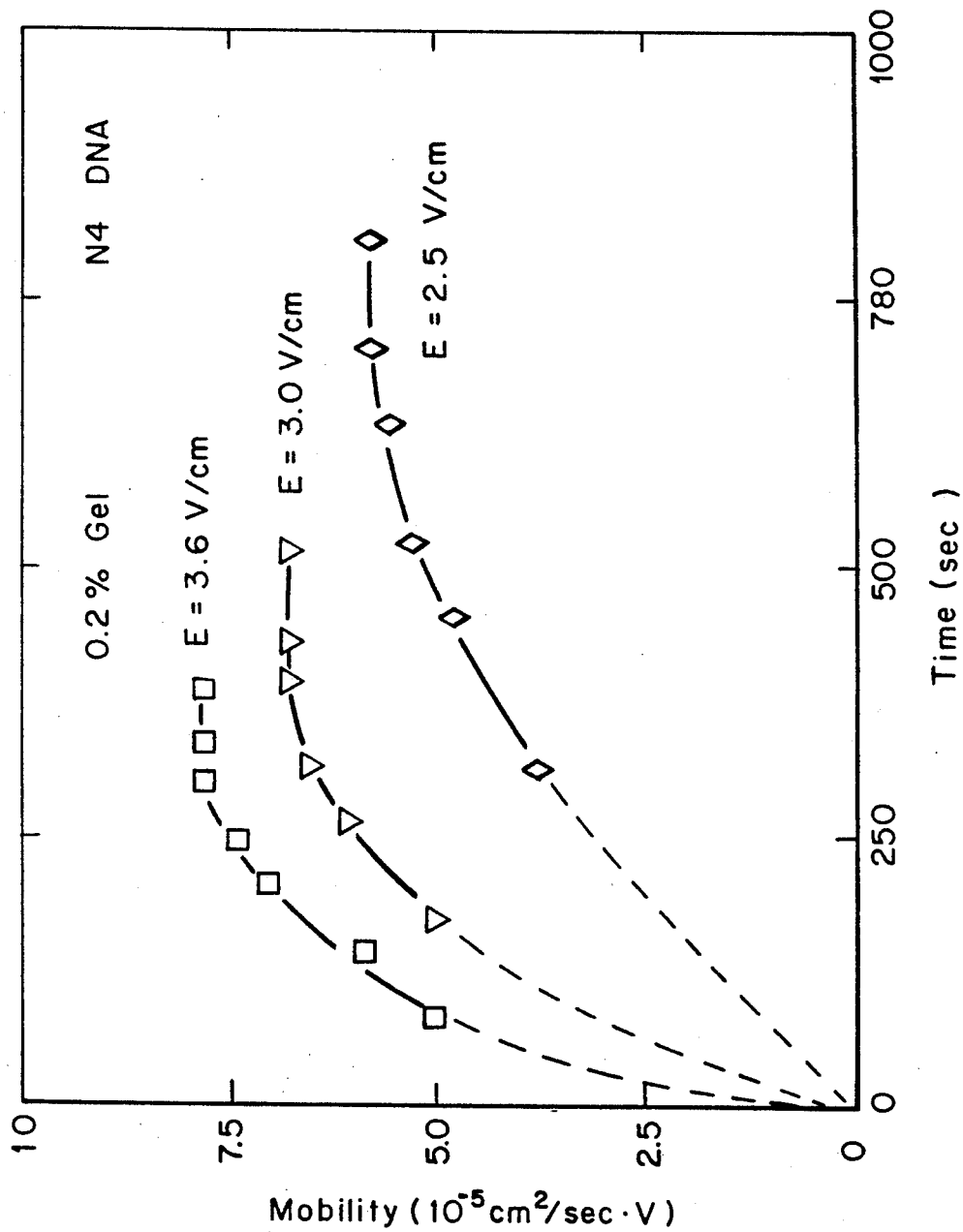

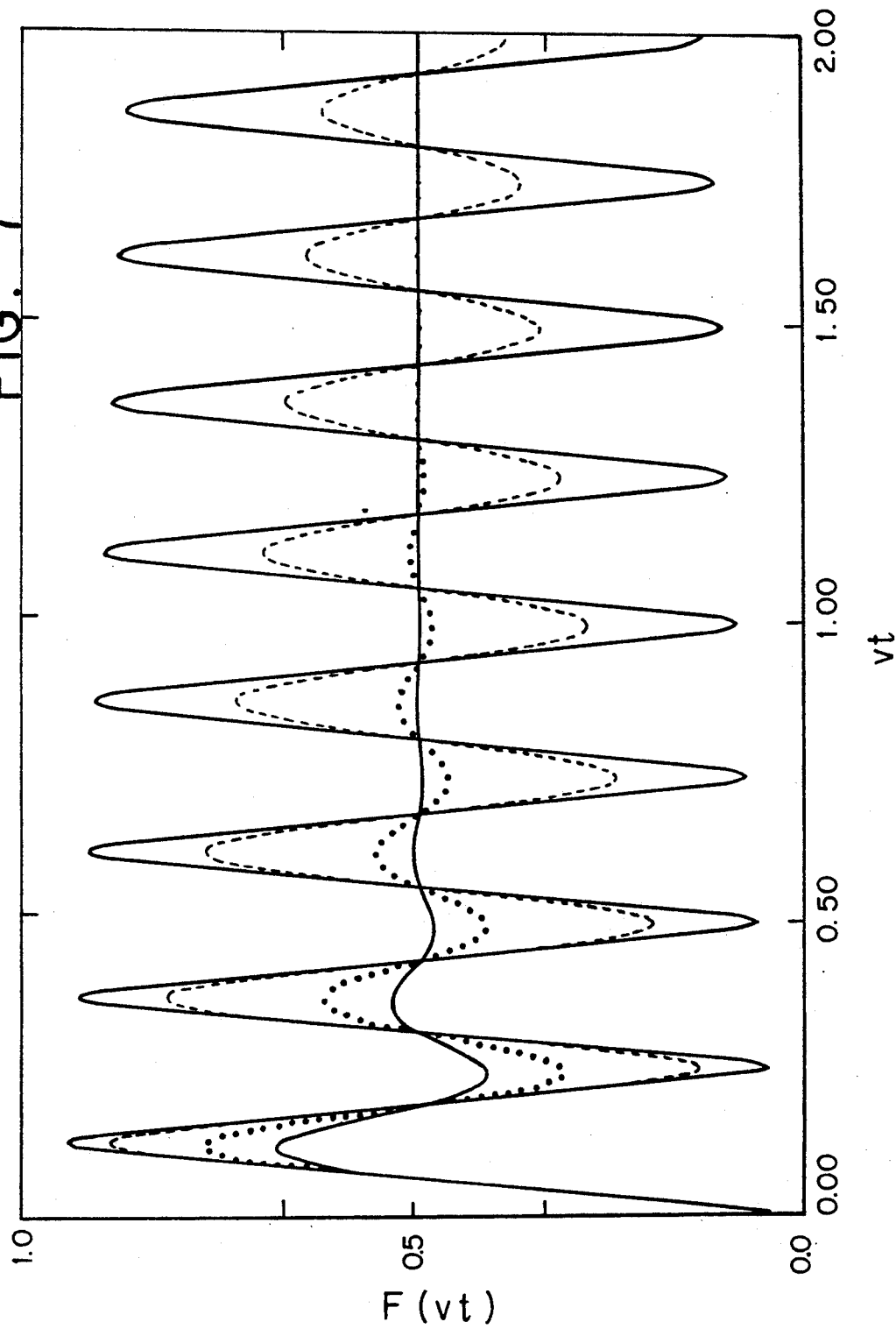

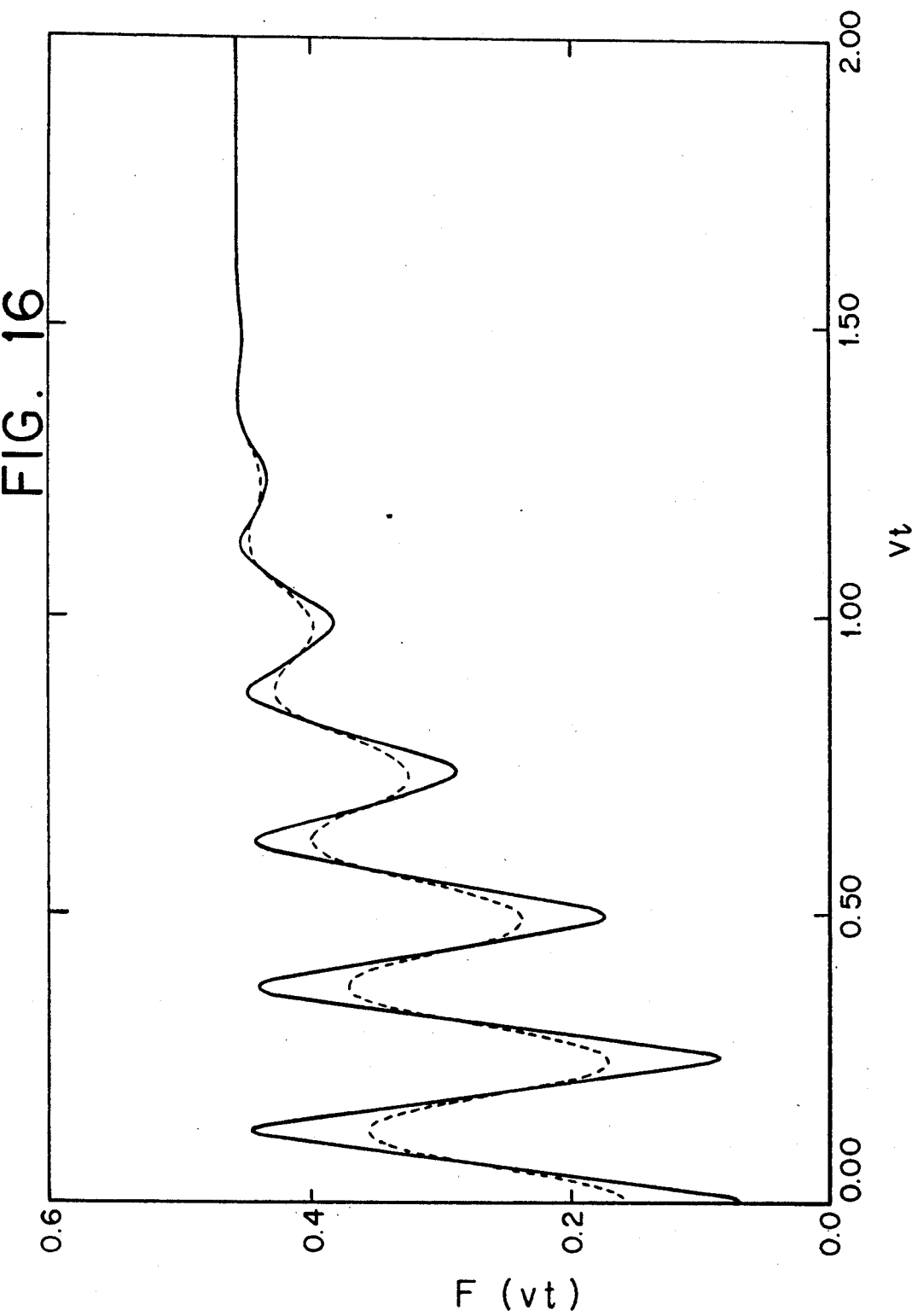

ELECTROPHORETIC MOBILITY OF FLUOROPHORE LABELED PARTICLES IN GELS BY FLUOROPHORE MOVEMENT AFTER PHOTOBLEACHING

This invention was partially made with Government support under the polymers program of the National Science Foundation DMR8617820. The Government has certain rights in the invention.

BACKGROUND OF THE INVENTION

1. Field of the Invention

This invention relates to a process and device for determining the electrophoretic mobility of fluorophore labeled nucleotide particles in gels by detecting fluorophore movement after photobleaching utilizing interference pattern produced by crossed laser beams or diffraction gratings having spacing in micron dimensions.

2. Background of the Related Art

Conventional gel electrophoresis has been a powerful analytic method for DNA separations. However, it is limited for effective fractionation of large DNA fragments up to about 20 kilo base pairs (kbp). Recently, Schwartz and Cantor, in *Cell*, 37, 67-75 (1984) introduced a pulsed-field gel electrophoresis (PFGE) technique, which allows separation of DNA molecules up to 2 mega base pair (Mbp). Modifications to the geometry of the applied electric field and other considerations to this technique have further improved the size resolution limit to 5~10 Mbp. See, Carle, et al., *Science*, 232, 65-68 (1986). The progress in PFGE electrophoresis has been reviewed by Cantor, et al. in *Ann. Rev. Biophys. Biophys. Chem.*, 17, 287-304 (1988).

In PFGE electrophoresis, one critical experimental parameter is pulse width (i.e., the time an electric field is applied in one direction before it is switched off or changed to another direction) which sets an upper limit on the DNA separation range. As pulse width approaches the DNA reorientation time, the electrophoretic mobility changes sharply with the molecular weight, and thus high resolution for DNA separation is achieved. Besides the pulse width, the separation resolution also depends on many other parameters, such as field strength, gel structure, DNA conformation and effective charge; other parameters include the geometry of the applied electric field, and the temperature. Therefore, if the parameters could be tuned to an optimum condition, the resolution could be improved and an even higher separation limit could be achieved. As a smallest human chromosome is estimated to be 30 Mbp (see, Anand, *Trends Genet.*, 2 278-283 (1986)) it appears that PFGE electrophoresis could become one of the major analytical tools for the human genome project. However, the details of the fundamental mechanism in this very important new technique remain semipractical at best. The parameters that influence the PFGE separation are numerous and coupled in a complex manner. Optimization of PFGE requires a thorough understanding of the dynamics of DNA chain deformation and corresponding electrophoretic motion in gels under an applied electric field. Chu et al. in *Biopolymers*, 27, 2005-2009 (1988), have studied orientation and stretching times of large DNA fragments in agarose gels by low-field electric birefringence (TEB). The low-field, long pulse width electric field birefringence measurements, however, could only provide information on DNA conformation dynamics including chain orientation and stretching.

A biased reptation model, as described by Lerman et al., *Biopolymers*. 21, 995 (1982); Lumpkin et al., *Biopolymers*, 21, 2315 (1982); Lumpkin et al., *Biopolymers*, 24, 1573 (1985); Slater et al., *Phys. Rev. Lett.*, 55, 1579 (1985), *Biopolymers*, 25, 431 (1986); Noolandi, et al., *Phys Rev. Lett.*, 58, 2428 (1987); and Hervet et al., *Biopolymers*, 26, 727 (1987), has been applied successfully to conventional gel electrophoresis (GE). Reptation theories have been further extended to include chain fluctuations; see Zimm, *Phys. Rev. Lett.*, 61, 2965 (1988); Noolandi et al., *Science*, 243, 1456 (1989). Recently, a numerical simulation proposed by Deutsch, in *Science*, 240, 922 (1988); *J. Chem. Phys.*, 90, 7436 (1989); and Deutsch et al., *J. Chem. Phys.*, 90, 2476 (1989), has provided a more detailed insight about DNA motion during PFGE and conventional GE. The suggested elongation-contraction chain behavior in an applied electric field has been used to explain the overshoot-undershoot phenomenon in fluorescence detected linear dichroism measurements; see Holtzwarth et al., *Nucleic Acids Res.*, 15, 10031 (1987). Observation of conformational changes of individual DNA molecules during gel electrophoresis by fluorescence microscopy supported the simulation results found by Deutsch; see, Smith et al. *Science*. 243, 203 (1989); and Schwartz et al., *Nature (London)*, 338, 520 (1989). Few directed experimental measurements have been reported, however, on the time-dependent electrophoretic mobility of DNA in gels while the DNA chains are being deformed, for example see, Holtzwarth et al., *Biopolymers*, 28, 1043 (1989).

Fluorescence recovery after photobleaching (FRAP) has been used for at least 15 years. Modifications to this method, including photobleaching a pattern instead of a simple spot on the sample and modulation detection of the fluorescence recovery signal, have been introduced to improve the ease with which FRAP can be applied to a variety of problems. See, for example, Smith & McConnell *Proc. Natl. Acad. Sci. USA*, 75, 2759-2766 (1978); Lanni & Ware, *Rev. Sci. Instrum.*, 53, 905-908 (1982); and, Wahl, *Biophys. Chem.*, 22, 317-321 (1985). Presently, FRAP has already become a common technique for measuring the mobility of specific components in complex systems, especially for the measurements of lateral mobility of lipid bilayers and of proteins in cell plasma membranes and cell organelle envelopes, as reported by Peters et al., *Biochim. Biophys. Acta.*, 367, 282-287 (1974); Axelrod et al., *Biophys. J.*, 16, 1055-1069 (1976); Jacobson et al., *Biochim. Biophys. Acta*, 433, 215-222 (1976); and, Koppel et al., *Biophys. J.*, 16, 1315-1325 (1976).

Diffusion and interaction of macromolecules in solution, as well as molecular motions in the cytoplasm and nucleoplasm can also be studied using FRAP. The idea for FRAP is simple and clear. The molecular species of interest are either fluorophores or molecules labeled with a fluorophore. Mobility of the fluorophores or of the fluorophore-labeled molecules is then measured by bleaching a spot (or pattern) on the sample with an intense pulse of light. The time for the fluorescence recovery, i.e., the dissipation of the bleached pattern, is a function of the size of the bleached area and the rate of mobility of the fluorophores or labeled molecules. The periodic pattern of photobleaching technique invented by Smith and McConnell (1978) supra., makes FRAP simpler in theory and in practice. The periodic pattern can be obtained either by using a diffraction grating (such as a Ronchi ruling) or by using two coherent crossed laser beams to produce an interference pattern. Two important aspects of the periodic pattern technique are its insensitivity to deviation of the bleached pattern from a pure spatial sinusoid, and its usefulness in detection of anisotropic diffusion in the image plane; see, Lanni et al., *Biophys. J.*, 35, 351-358 (1981).

U.S. Pat. No. 4,222,744 to McConnell describes in general terms an assay for label ligands such as fluorescent labeled nucleotides in which the mobilities of the ligands are detected by observing fluorescence recovery after photobleaching of the labeled ligands. The ligands are bleached using a single laser focused to a spot in a fluid or gel or using a laser generated pattern of lines.

U.S. Pat. No. 4,675,095 to Kambara describes an electrofluoretic apparatus for detecting electrofluoretic labeled nucleotides after excitation by a single light source, such as a laser. The disclosure is specifically directed to the production of low background noise by exciting the fluorophore labeled nucleotides by incident excitation light projected in the gap between the two glass plates substantially parallel to the boundary planes of the gel. Fluorescence is detected in a direction perpendicular to the excitation light source.

Similarly, U.S. Pat. No. 4,832,815 to Kambara et al. cites the Smith et al. article in *Nature* (1986) supra., for the disclosure of a system in which a DNA fragment is detected in real time during electrophoresis separation through fluorescent labeling of the DNA. The DNA fragments are irradiated with a laser and when they pass through the irradiated region they give forth fluorescence successively from the shortest fragment. Since the emission wavelengths differ depending upon the base species, the base species are determined from the wavelengths. The lengths of the frame can thus be determined from the migration times.

Likewise, U.S. Pat. No. 4,832,815 describes a wavelength dispersion electrophoresis apparatus which detects fluorescence of unequal wavelengths emitted from samples of nucleotides which are labeled with a plurality of fluorophores. A single laser beam is used to excite the fluorophores at a particular location in the gel while a direct-vision prism is interposed between the two dimensional fluorescence detector and electrophoretic plate in order to separate and discriminate the emission wavelengths of the respective fluorophores.

Capillary electrophoresis has been used to detect the separation of nucleic acids in a very small volume, as reported by Kasper et al., *J. Chromatogr.*, 458, 303-312 (1988). Kasper et al. describe experiments using absorbance and fluroscence detectors modified for use with a 50-100 $\mu$m inside diameter (I.D.) capillary tubing. The instruments were tested, and a signal to noise ratio of 3 was observed in measuring 15 $\mu$g/ml for fluorescense detected of ethidium bromide-stained herring-sperm DNA and 3 $\mu$g/ml for absorbance detection, at a separation voltage of up to 30 kV.

Electrophoretic mobilities of photochromically labeled ions have been measured by combining electrophoresis with holographic relaxations spectroscopy (HRS) or forced Rayleigh scattering (FRS), as reported by Rhee et al., *J. Phys. Chem.*, 88, 3944-3946 (1984); and Kim et al., *J. Phys. Chem.*, 88, 3946-3949 (1984). The species of interest in HRS or FRS, however, have to be photochromic or labeled with photochromic dyes whose lifetimes are longer than the relaxation time of interest. Unfortunately, in differentiating and determining the dynamics of large DNA fragments, the lifetimes of most photochromic dyes are too short when compared with the time required to measure the slow DNA electrophoretic mobility in gels. The related art, therefore, does not describe techniques for very rapidly measuring the electrophoretic mobility and dynamics of large DNA particles.

Accordingly, it is an object of the present invention to provide a technique for very rapidly determining the mobility of polyelectrolytes, especially large DNA fragments in gels.

SUMMARY OF THE INVENTION

These and other objects are achieved by the present invention which provides a process and apparatus for detecting the mobility of fluorescent labeled molecules in response to a force. The fluorescent labeled molecules can include fluorescent labeled DNA or protein molecules, or they may include other fluorescent labeled molecules or particles. Accordingly, fluorescent labeled molecules are placed in retaining means, such as a gel medium, sample cell or capillary in a fluid medium. A sample cell or capillary preferably contain a substrate for electrophoresis, such as a gel or micelles. A force is imposed on the labeled molecules, preferably an electrical potential difference for causing electrophoretic movement and separation of the fluorescent labeled molecules in the gel or fluid medium.

Labeled molecules or particles are photobleached in the fluid medium, leaving a first geometrically defined region which has not been photobleached. The first geometrically defined region of the labeled molecules or particles in the fluid medium is excited with a reading beam which has a second geometrically defined configuration of light and dark. The photobleaching and the reading beam can suitably be accomplished by using a laser focused through a diffraction grating which produces a pattern of light and dark. Preferably, the photobleaching and the reading beam can be achieved by using a high intensity light focused through a mask. Additionally, the photobleaching and the reading beam can be accomplished by crossing two laser beams forming an interference pattern. The intensity produced by the interaction of the second geometrically defined configuration of the reading beam and the movement of the first geometrically defined region of the unbleached labeled molecules is detected by a photo detector such as a PMT.

In detecting more than one species of labeled molecules, the reading beam which has the second geometrically defined configuration is modulated as a function of the velocity of the labeled molecules through the fluid medium and the frequency of the resulting intensity pattern produced by the interaction of the modulated (oscillating) reading beam and the movement of the labeled molecules through the fluid medium are analyzed.

For a better understanding of the present invention, reference is made to the following description and examples, taken in conjunction with the accompanying tables and drawings, the scope of which is pointed out in the appended claims.

BRIEF DESCRIPTION OF THE DRAWINGS

FIG. 3 (b) shows a time-dependent mobility profile derived from the fluorescence intensity traces in graph (a), as described in Example 4.

FIG. 4 (b) is a plot of steady-state mobility $\mu_s$ vs. $E^2$ for N4 DNA-EB in 0.2% and 0.4% agarose gels, as described in Example 5.

FIG. 6 (b) shows the fluorescence intensity trace vs. electric-fields-on time for λ DNA-EB in 0.2% agarose gel E=2.9 V/cm, as described in Example 7.

FIG. 7 is a graph showing the calculated F(vt) with different values of D/v vs. vt by using equation (12), where it is assumed that $C_o=1$, $r=1$, $\Delta C=1$, $I_{o,r}=1$, $\alpha=1$ and L=0.25, as described in Appendix A. The solid line is for $D/v=10^{-4}$, dashed line for $D/v=10^{-3}$, dotted line for $D/v=5\times 10^{-3}$ and broken for $D/v=10^{-2}$.

FIG. 16 is a graph showing the calculated values of F(vt) vs. vt by using different methods to produce a periodic pattern. The solid line is by means of a Ronchi Ruling. The broken line is by crossing the two laser beams. $C_o=1$, $r=1$, $\alpha=1$, $I_{B,r}=0$, $I_{o,r}=1$, $C_B=0$, $\Delta C=1$ and $D/v=10^{-4}$.

DETAILED DESCRIPTION OF THE PREFERRED EMBODIMENTS

Figure 1:
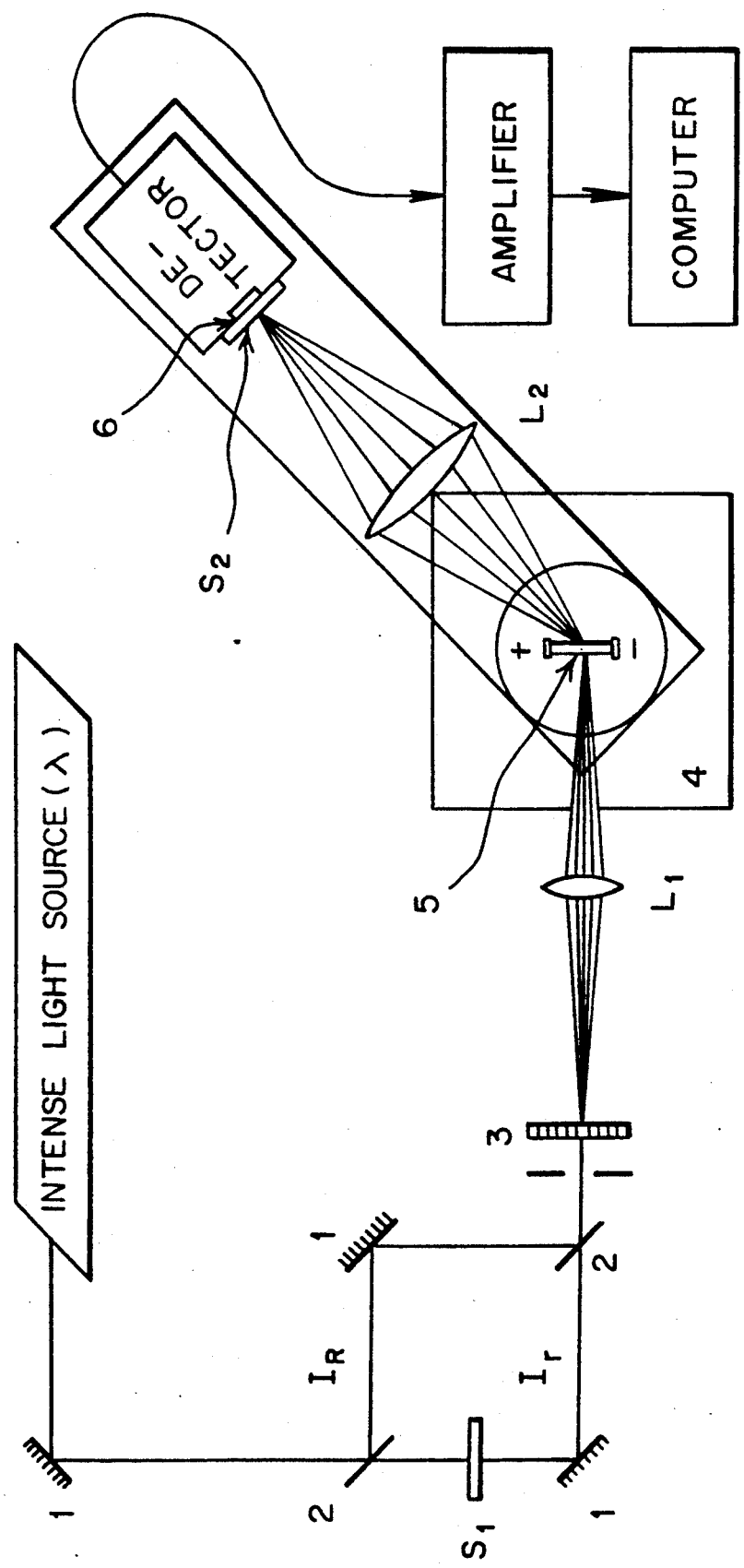
FIG. 1 is a schematic diagram of an EMOFPAP apparatus in accordance with the present invention.

According to the present invention, a method and apparatus is provided which utilizes gel electrophoresis with movement of fluorescence pattern after photobleaching, abbreviated EMOFPAP. Using the present invention, the electrophoretic mobilities of large DNA fragments have been measured in an agarose gel, within a fairly short time scale, about 10 minutes or even down to about 1 minute. The method of the present invention presents significant improvement in assay time, when compared with the time, typically on the order of hours, required to determine the average electrophoretic mobility of large DNA fragments in agarose gels by using either conventional gel electrophoresis (GE) or pulsed-field gel electrophoresis (PFGE). The present invention describes the EMOFPAP apparatus and method, the optical conditions, including the beam profile geometry and fluorescence pattern formation. A realistic formula that explains the parameters governing the EMOFPAP method of the present invention using the disclosed apparatus has been derived. A comparison of results between experimental results and computer simulation data is presented and optimization of the EMOFPAP method of the present invention is described.

The EMOFPAP method of the present invention provides equally important information on DNA electrophoretic mobility on an almost instaneous time scale, i.e., over time intervals of minutes as compared to hours in standard GE or PFGE. The present invention, therefore, provides a means for examining DNA dynamics in gels and capillaries on a much shorter time scale. The examples utilize the EMOFPAP method and apparatus of the present invention to determine the electrophoretic mobility of α DNA and of N4 DNA in agarose gels. In these examples, the electrophoretic mobilities of large DNA fragments are determined in agarose gels on a time scale of ~10 minutes, or even down to ~1 minute, instead of the hours it takes to make the same determination using standard gel electrophoresis or PFGE. Additionally, the present invention provides the ability to examine the DNA electrophoretic mobility during different stages of DNA deformation in the presence of an applied electric field or immediately after the field has been turned off.

In the examples, the EMOFPAP method of the present invention has been demonstrated by using the periodic pattern florescence photobleaching of ethidium bromide (EB) labeled large DNA fragments in an agarose gel and subsequent observations of the electric field induced phase modulation due to the electrophoretic drift of labeled large DNA fragments. A modulation of flurorescence emission is produced as the photobleached pattern moves in and out of phase with the illumination pattern. The resulting photocurrent contains an AC component whose frequency is determined by the fringe spacing and the electrophoretic mobility of large DNA fragments. In the examples, the photocurrent was recorded and the drift frequency was determined for a known fringe spacing. In this manner, the mobility of large DNA fragments is determined. Stationary electrophoretic mobility determined by the method of the present invention was in agreement with values obtained by conventional gel electrophoresis. In comparison with conventional or pulse-field electrophoresis, a major and distinct advantage of the method of the present invention is the very short measurement time on the order of a few minutes or less instead of several hours needed to determine the electrophoretic mobility of large DNA fragments. The short measurement time permits an investigator to follow changes in the electrophoretic mobility of large DNA fragments after application or upon termination of an electric field. By contrast, ordinary gel electrophoresis and PFGE can only measure an average electrophoretic mobility over periods of hours.

Accordingly, the EMOFPAP method and apparatus of the present invention is able to measure the electrophoretic mobility of one or more species of large DNA fragments in agarose gels within a very short time scale and provide a new opportunity to understand DNA dynamics on a more instantaneous scale.

By using the EMOFPAP method of the present invention, the electrophoretic mobility of EB-labeled ($\lambda$ or N4) DNA molecules have been successfully determined over very short distances and accordingly, in very short time periods, i.e., $\sim 1$ to 10 minutes in an agarose gel network. The changes in the initial mobilities, measured by using the EMOFPAP method of the present invention, indicate that conformational stretching and alignment processes of DNA molecules in the initial stage of an applied electric field have measureable effects on the DNA electrophoretic mobility.

In performing the EMOFPAP method of the present invention, it should be understood that for large DNA molecules and agarose gels, the self-diffusion is very slow and can be ignored when compared with electrophoretic mobility even at very low field strengths. In the EMOFPAP method of the present invention, the recovered fluorescence intensity signal is directly related to the movement of the fluorescent molecules. As illustrated in the examples, the bleached periodic pattern of the sample moving in and out of phase with the space-fixed periodic monitoring pattern of laser light results in a sinasoidal intensity trace. One period in the intensity trace represents moving the bleached pattern over one spatial period of the periodic monitoring pattern. Accordingly, the short-time-averaged electrophoretic mobility can be deduced from the time period $t_p$ of the intensity trace by the relation $$\mu = v/E = L/t_p E \quad (1)$$

with v, L, and E being the drift velocity, the spatial period of the periodic pattern, and the electric field strength, respectively. The short-time ($\sim$min) averaged mobility, instead of the terminal mobility, can provide information on the time-dependent electrophoretic mobility of large DNA molecules in gels while the DNA chains are being deformed.

In separating large particles, or molecules such as proteins or DNA fragments, investigators have used fluorescent labels in order to follow the movement of these particles or molecules. Various size molecules or fractions may exist in a sample, and each of these fractions may move at a different rate through a gel or capillary. A key aspect in using the present invention, is the ability to produce a fine line of demarkation on a portion of these labeled molecules by photobleaching away the fluorescent label, such as (EB), about this line of demarkation. The results of photobleaching around this line of demarkation, typically using a high intesity laser, allow most of the sample being separated (such as different fragments of fluorescent labeled DNA molecules which may be contained in a region of $\sim 1$ millimeters in width) to be masked. Only the labeled material within the very narrow line of demarkation, for example, 10 microns in width which has not been photobleached, then becomes the sample of interest to be detected.

Accordingly, in PFGE in order to have a resolution effect of 100 for adequate separation of an aliquot 1 millimeter in width, the aliquot must be moved by a factor of 100, i.e., 100 millimeters or 10 centimeters. Normally, GE or PFGE takes on the order of hours, typically from $\sim$5 to 10 hours to move such a region of DNA 10 centimeters.

By using a fine line of demarkation which is limited only by the wavelengths $\lambda$ of the incident light source ($\sim$5 microns), preferably in the range of from $\sim$1 to $\sim$20 microns, for example, $\sim$10 microns, even though the molecules of different sizes are still present in the region after a very short period of time, the width being examined is 10 microns instead of a millimeter. Therefore, the separation base becomes 10 microns instead of 1000 microns (=1 mm). Accordingly, the distance the 10 micron wide line of demarkation must travel to achieve the same resolution discussed above for the 1 millimeter region is reduced by a factor of 100.

The line or lines of demarkation may be produced by two crossed laser beams forming an interference pattern, by a laser focused through a diffraction grating which produces a pattern of light and dark, or by an intense light shining through a mask. The mask could also be a diffraction grating. The intense light may be produced by a laser or it may be produced by other intense light sources such as a mercury arc lamp.

If, there are more than a one species of molecules moving at different rates under the applied electric field, if one species moves at the rate of 100 millimeters in an hour and the other species moves at the rate of 1 millimeter in an hour, $\sim$1 hour would be needed to satisfactorily detect both species from an aliquot 1 mm in width. However, by using the present invention, if the unbleached line of demarkation is only 10 microns wide, much smaller distances would be needed to distinquish the two species, without of course, changing the velocity of the species under the applied electric field. In this manner, the present invention allows analysis of the velocity of molecules over much shorter periods of time, and therefore the movement of the molecules can be analyzed as they are changing or deforming over short time periods.

In addition, if there are many species of molecules in the sample it is possible to distinguish the electrophoretic mobility of a number of different species by utilizing a diffraction grating and by performing a frequency analysis. In order to perform frequency analysis efficiently, a diffraction grating containing many lines of demarkation must be used. This photobleaching pattern creates a superposition of molecular fluorescent grating which move at different speeds. A reading beam produced by a grating is imposed on the fluorescent grating of the molecules moving at different velocity, by oscillating the reading grating at frequencies which match the velocity of the fluorescent grating of the molecules, various species can be distinguished. Thus, by performing a mathematical analysis of these frequencies, called a frequency decomposition, the movement of each of these species can be determined.

For example, if there are two species moving at different velocities a single detection pattern can be imposed and moved at the same rate that one of the species migrates. This pattern would cancel out a signal of the one species and allow detection of the other species. If the pattern is isolated at a predetermined speed which matches the movement of the first species, the second species can be detected over very small distances by utilizing frequency or interference analysis.

The EMOFPAP method and apparatus of the present invention can be used with suitable SDS gel electrophoresis techniques, or it can be used with capillary electrophoresis using, for example, gels or SDS micelles as a medium or complexing agent, respectively. Capillary electrophoresis separation techniques are described in detail by Kasper et al., in *J. Chromatoqr.*, 458, 303-312 (1988), the description of which is incorporated by reference herein. Capillary electrophoresis typically utilizes 50-100 μm inside diameter (ID) fused silica capillary tubing. The instruments used by Kasper et al., had a signal to noise ratio of about 3, and used a power supply producing a voltage of up to 30 kV.

Accordingly, the method of the present invention can be used to impose a photobleached pattern or line of demarkation onto DNA fragments in a capillary to decrease the time of separation by orders of magnitude, dramatically reducing the length of the capillary tubing and the magnitude of the high voltage while maintaining the same field strength.

The following examples further illustrate the various features of the present invention, and are not intended to limit the scope of the invention which is defined in the appended claims.

EXAMPLE 1

Instrumentation

A schematic diagram of the EMOFPAP apparatus is shown in FIG. 1. It is typical of an FRAP experimental setup described by Wahl, *Biophys. Chem.*, 22, 317-321 (1985). The difference is that the sample holder has been modified in order to carry out electrophoresis at the same time. In this Example the intense light source is an Ar ion laser having a wavelength of 488 nm, and as shown in FIG. 1, the apparatus includes mirrors 1, flat optical glass plates 2, means for illuminating a defined boundery of light and dark 3, which in this example is a Ronchi Ruling, displacement means for displacing the sample cell which in this example is turn table with stepping motor 4, sample cell 5 in this example $30 \times 6 \times 0.6$ mm, low-pass and rejection filters 6, in this example 488 nm rejection filters, and Lenses $L_1$, $L_2$. A 3 Watt argon-ion laser (Spectra-Physics 2020-03) was used for both photobleaching (or writing) and the observation (or reading) beams.

A flat optical glass plate 2 splits the incident laser beam into two beams, one ($I_W$) passing through the glass and the other ($I_R$) reflected by the glass. The subscripts R and W denote reading and writing beams, respectively. The intensity ratio of the two beams $I_W/I_R$ is about 96:4. $I_W$ and $I_R$ are recombined by means of mirrors 1 at the second optical glass plate 2. The intensity ratio between the two recombined beams $I_w$ and $I_r$ is about $1:10^{-3}$, since $I_R$ undergoes a second reflection to yield a much weaker reading beam ($I_r$). The subscripts r and w denote the final reading and writing beams. For the following examples, the power density for $I_w$ and $I_r$ were 10 W/cm$^2$ and 10 mW/cm$^2$, respectively. It should be noted that these examples measure mainly the movements of unbleached DNA molecules that are labeled with ethidium bromide. Thus, the effect by the photochemical scission of DNA should be minimal. Computer-controlled shutters, $S_1$ (UniBlitze SD-10) and $S_2$ (UniBlitze SD-1000), are designed so that they will not open at the same time in order to protect the detector (i.e., a photo multiplier tube detector) (PMT). During the photobleaching process, $S_1$ is in the open position and $S_2$ is closed. During the reading process, $S_1$ is closed and $S_2$ is switched to the open position.

The present invention can use a diffraction grating, or a mask with one or more evenly spaced or staggered lines such as Ronchi Ruling 3 with a frequency of 100 lines/inch (Edmund Scientific Co.) which produces a periodic pattern with size spacing L of 254 or 127 μm to a thin (0.6 mm) sample chamber or capillary tube, as illustrated in FIG. 1. Thus, a real image having alternatively bright and dark fringes of the grating or mask is projected onto the sample. Alternatively, the present invention can use a beam splitter to split both $I_w$ and $I_r$ into two equal-intensity coherent laser beams and then crossing them to form a periodic interference pattern.

Different fringe spacings can be achieved easily by varying the position of the first lens ($L_1$, a high-quality complex lens). After bleaching, $S_1$ is closed, which triggers $S_2$ to open. Fluorescence emission are collected into the PMT by the second lens ($L_2$), which has a large diameter (70 mm) and a short focal length (50 mm). One rejection filter (reject peak position at 488 nm) and one low-frequency-pass filter have been combined to prevent $I_r(\lambda_0 = 488$ nm) from leaking into the PMT in order to reduce the background noise. The photocurrent from the PMT (Hamamatsu R928) is amplified by an amplifier (Thorn EMI A-1). Depending on the electrophoretic mobility and fringe spacing, the amplified signal can be recorded either by an IBM-PC/AT computer through an IBM data acquisition card (12-bit resolution) or by a multichannel recorder (Biomation 8100). The timing of the applied electric field and of the EMOFPAP measurement are adjustable and controlled by the same IBM PC/AT computer.

EXAMPLE 2

Sample Preparation

Two large DNA molecules, N4 (71 kb) DNA and λ(48.5 kb) DNA (where kb denotes kilo base pairs), were purchased from New England Biolabs. The stock solution was composed of 10 mM Tris buffer (pH 8.0), 1 mM EDTA, and 500 μg/mL DNA, and was stored at about −20° C. The ultrapure electrophoresis grade agarose powder with low electroendosmosis was purchased from Bethesda Research Laboratories. The DNA molecules were labeled with trace amounts of EB (i.e., ~0.005% to ~0.5 of base pairs per each DNA molecule were stained with EB molecules). For preparation of the DNA-EB/agarose gel solution, a known amount of agarose powder was dissolved into a known volume of distilled deionized water by boiling in a microwave oven. The amount of water evaporated during boiling was corrected. Then, the gel solution was transferred to an oven that was set at a constant temperature 55°≈60° C. for equilibration. The DNA-EB solution was mixed with the gel solution at about 35° C., and then the mixture was pipetted at very low shear rates into the sample cell (35×6×0.6 mm). The final DNA and agarose gel concentration was about 15 μg/mL, and two gel concentrations, 0.2 and 0.4%, were used. All experiments were conducted at a temperature of 23°±0.1° C.

EXAMPLE 3

Figure 2:
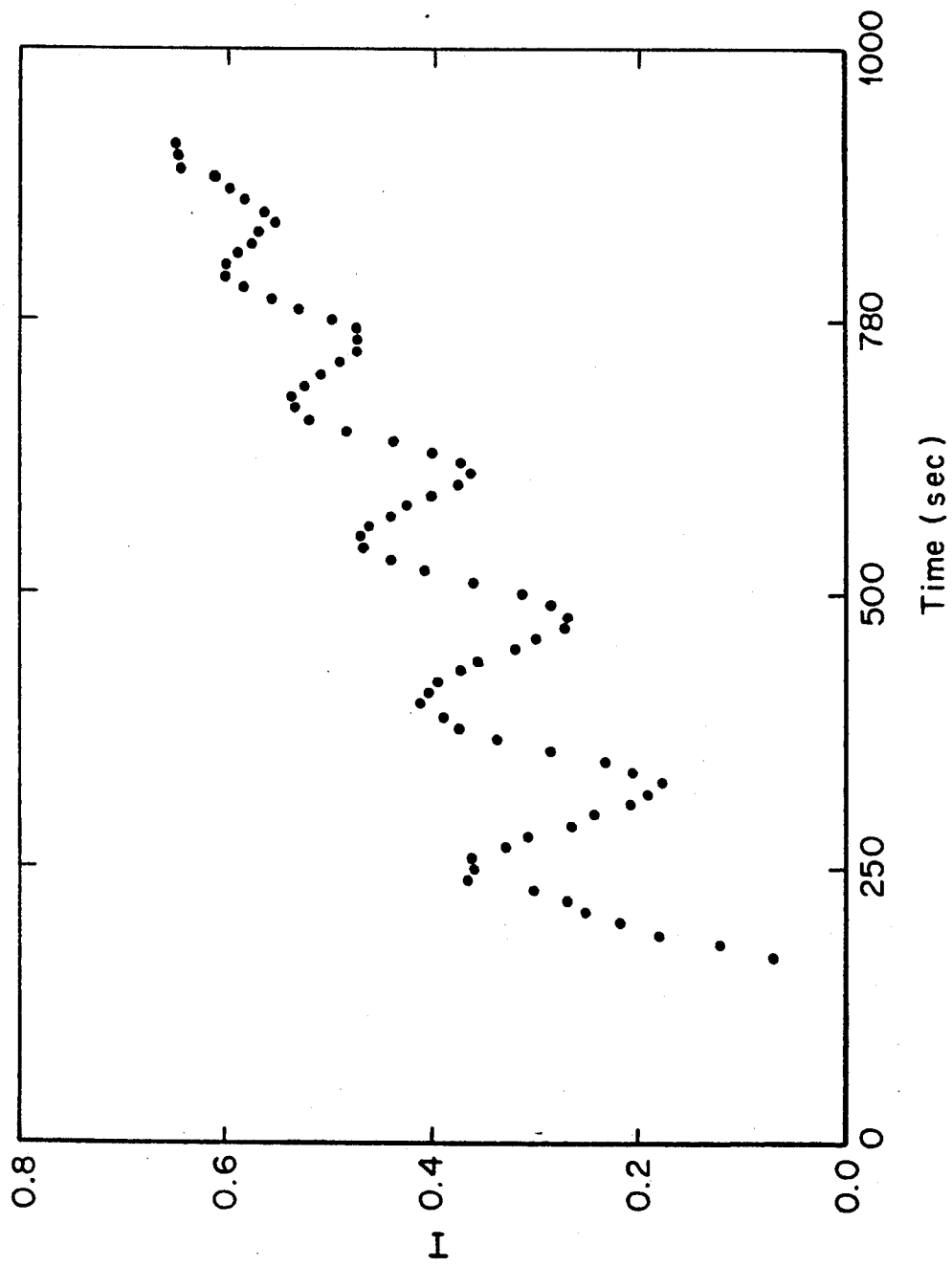
FIG. 2 is a graph showing a fluorescence intensity signal from a moving fluorescence periodic pattern of λ DNA-EB (size=48.5 kbp) in 0.2% agarose gel and an electric field strength E of 2.9 V/cm, described in Example 3.

A fluorescence intensity signal from a moving fluorescence periodic pattern for λ DNA-EB in 0.2% agarose gel at a field strength of 2.9 V/cm was determined using the apparatus and samples described in Examples 1 and 2. The electric field was applied immediately after photobleaching. A graph showing the fluorescence intensity vs. time is shown in FIG. 2. The net fluorescence intensity I is in arbitrary units. The DNA concentration $C_{DNA}=15\mu g/mL$ in 0.3 mM Tris buffer and 0.03 mM EDTA. The stationary mobility $\mu = 7.3 \times 10^{-5}$ cm$^2$/s−V.

The modulation of the bleached fluorescence periodic pattern is a cosine function with a basic frequency as described by Lanni, et al., *Rev. Sci. Instrum.*, 53, 905–908 (1982)

$$\omega = (2\pi/L)v \qquad (2)$$

where L is the spatial period of the fringe pattern and v is the drift velocity. Thus, the mobility $\mu=v/E$, with E being the applied electric field strength, could be calculated by measuring the period of the redistribution of fluorescence intensity. In FIG. 2, the time period in the phase modulation of the moving fluorescence pattern decreases and approaches a constant value of about 120s after 2 to ~3 relatively longer periods. The stationary mobility was ~7.3×10$^{-5}$ cm$^2$/s−V, in good agreement with the gel electrophoresis mobility, as reported by Fangman, *Nucleic Acids Res.*, 653–665 (1978), which represents a macroscopic net result after a long running time of 10 hours with the electric field on. The mobility of λ DNA in 0.4% gel is ~5.3×10$^{-5}$ cm$^2$/s−V at the same field strength of 2.9 V/cm. The depth of modulation reached ~60% instead of 100%, mainly because of imperfections in the periodic writing and reading patterns. In addition, the depth of modulation is decreased by a variety of factors, such as finite beam dimensions and nonuniform beam profiles.

In this example, there is ~8% uncertainty in determining the mobility, which could be improved. The orientation and stretching of DNA molecules along the field direction cause the initial nonstationary stage. Before the DNA molecules achieve a saturation alignment and stretching that are limited by the field strength and pulse duration, the orientation and the translational movement occur simultaneously, Therefore, movements of bleached fluorescence patterns could yield the net mobility of DNA molecules in gels at each stage (before, during, and after) of DNA orientation/stretching. The term "after" refers to the field-free relaxation back to the DNA equilibrium conformation. Although intercalation of even small amount of the EB dye into the base pairs of DNA molecules can stiffen the DNA chain, it does provide an appropriate demonstration. The DNA mobility can be studied as a function of EB concentration. Nonintercalating fluorescence dyes suitable for DNA labeling are also available. The orientation and stretching processes could be studied in more detail by changing the spacing and orientation of the fringe pattern, including the use of crossed laser beams, as discuss above, instead of Ronchi transmission ruling.

This example shows that for the first time the electrophoretic mobility of large DNA fragments (e.g., λ DNA) has been determined in agarose gel by using the EMOFPAP technique. The DNA mobility in gels could be obtained in about 15 min with the present fringe period spacing (~254 μm) rather than the usual 10 hours by conventional gel electrophoresis or PFGE electrophoresis. More importantly, the orientation and stretching processes can be correlated with the time-dependent electrophoretic mobility.

EXAMPLE 4

Figure 3A:
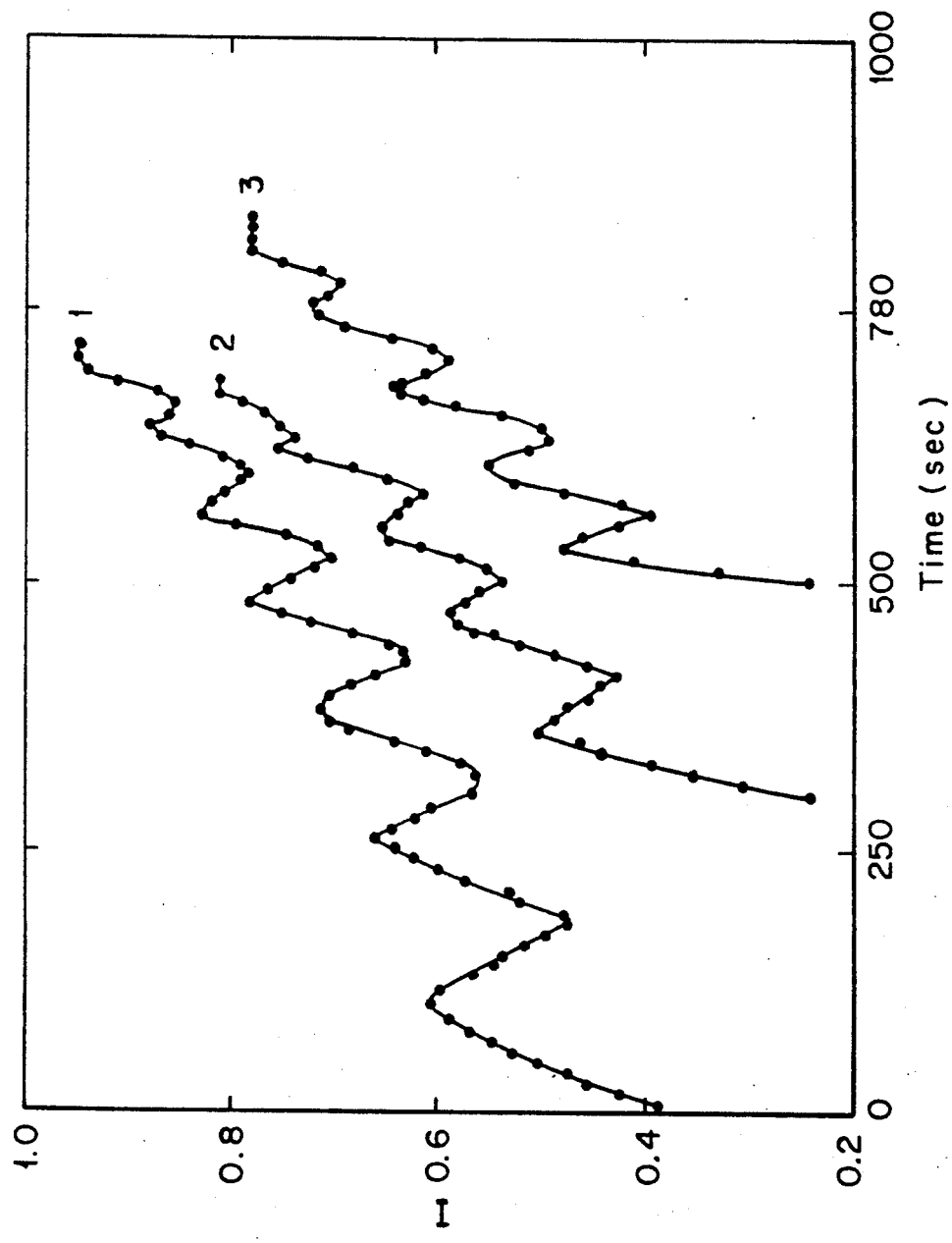
FIG. 3 (a) shows three fluorescence intensity traces vs. electric field-on time of λ DNA-EB in 0.6% agarose gel at E=3.5 V/cm, as described in Example 4.

The conditions of the EMOFPAP described in Example 3 were modified to use a 0.6% agarose gel at E=3.5 V/cm. FIG. 3 at graph (a) shows three fluorescence intensity (I) traces vs. electric-field-on time from EMOFPAP measurements under these conditions. Curve 1 denotes the fluorescence intensity trace in which the electric field was applied immediately after photobleaching. The time $t_p$ decreased with increasing field-on time, and then reached a plateau value with further increase of field-on time. Curve 2 represents the photobleaching of EB-labeled DNA at about 300 seconds after the applied electric field has been turned on. The decrease in $t_p$ indicates that the electrophoretic mobility of DNA molecules increased with the initial field-on time and $t_p$ finally reached a steady-state value as shown in FIG. 3 at graph (b). FIG. 3 at graph (b) shows the time-dependent mobility profile derived from the fluorescence intensity traces in graph (a). Triangles, squares, and diamonds denote the mobility values from curves 1,2, and 3, respectively.

To prove that these results could be reproduced, the electric-field was applied for a certain long time ≥300 seconds for curve 2, and 500 seconds for curve 3, before photobleaching. The mobility data obtained can be fitted by one curve as shown in FIG. 3 at graph (b). The short-time-average mobility over a moving distance of 254 or 127 μm revealed an electric-field-on time dependence that could not be observed by conventional GE or PFGE.

These results show that the mobility is independent of when the photobleaching takes place, and confirm the dependence of the mobility on the electric-field-on time. Thus, these results provide evidence which shows that instead of keeping the original conformations, DNA molecules experience a deformation and then achieve an equilibrium but stretched conformation in an applied electric field. The deformation changes the electrophoretic mobility of DNA and should be responsible for the separation resolution loss of large DNA fragments. Establishing the relationship between DNA electrophoretic mobility and chain deformation should be an important factor in PFGE.

EXAMPLE 5

Figure 4B:
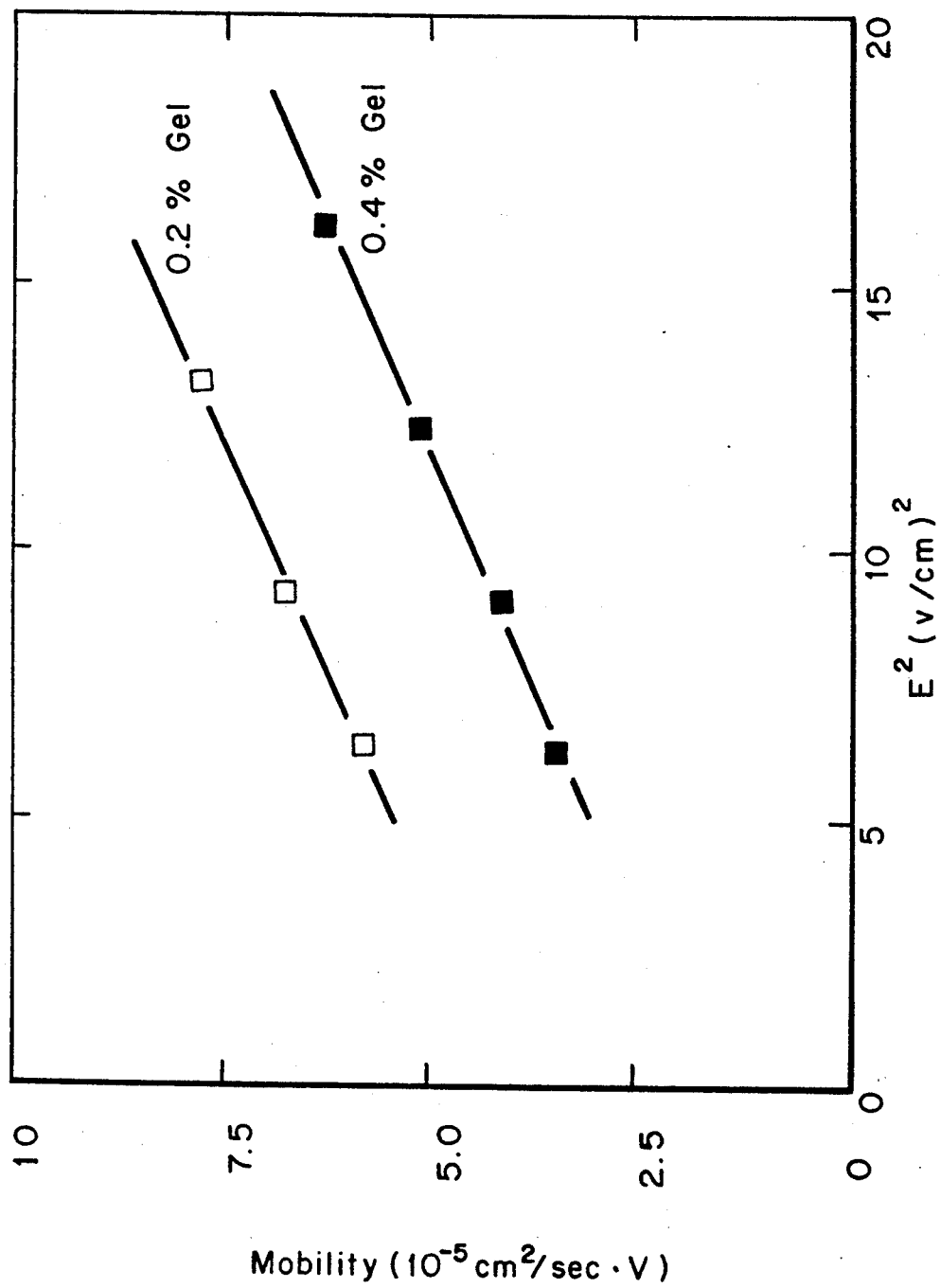
FIG. 4 at graph (a) shows the effect of electric field stength on time-dependent mobility for N4 DNA-EB in 0.2% agarose gel, as described in Example 5.

The effect of electric field strength on time-dependent mobility for N4 DNA in 0.2% agarose gel and 0.4% agarose gels were tested under various electric fields strengths of E=3.6 V/cm, 3.0 V/cm and 2.5 V/cm. FIG. 4 at graph (a) shows the effect of increasing electrical field strength on time-dependent mobility for N4 DNA in 2% agarose gel. FIG. 4 at graph (b) plots the steady-state mobility $\mu_s$ vs. $E^2$ for N4 DNA in 0.2% and 0.4% agarose gels. The lines denote the linear-least-squares-fitting results. The extrapolated mobility values, $\mu_s(E\rightarrow 0) = 4.0 \times 10^{-5}$ and $1.6 \times 10^{-5}$ cm$^2$/V sec for 0.2% and 0.4% agarose gels, respectively, are in reasonable agreement with conventional gel electrophoresis results published by Slater et al., *Biopolymers*, 27, 509 (1988).

In conventional GE, the electrophoretic mobility is a function of DNA molecular weight, gel concentration, electric field strength, temperature, ionic strength, viscosity of buffer, etc. Concerning the electric-field-strength effect, the biased reptation theory provides a simple formula in the limit of low-field strength, $$\mu = \frac{Q}{3\xi}\left(\frac{1}{N_t} + \frac{E'^2}{3}\right), \quad (3)$$

where Q and $\xi$ are, respectively, the total charge and the friction coefficient of the chain, $N_t$ is the number of tube segments, and $E' = qaE/2k_BT$ is a dimensionless reduced electric field strength with q and a being the effective charge and the tube length of one segment, respectively. The strong dependence of the electrophoretic mobility upon the electric field strength predicted by the theory was confirmed by conventional GE, see Slater, et al. (1988), supra. FIG. 4 at graph (a) shows the observed field-strength effect on the measured mobility during the initial field-on time. As shown in FIG. 4 at graph (a) with the field strength increased, the magnitude of the steady-state mobility $\mu_s$ increased and the time-dependent mobility $\mu$ reached the steady-state (saturation) value over a shorter field-on time. A linear dependence of $\mu_s$ on $E^2$ was also observed, as shown in FIG. 4 at graph (b), in qualitive agreement with equation (3). Furthermore, the extrapolated mobility $\mu(E\rightarrow 0)$ values, i.e., $1.6 \times 10^{-5}$ and $4.0 \times 10^{-5}$ cm$^2$/V sec for N4 DNA in 0.4% and 0.2% agarose gels, respectively, are in reasonable agreement with the conventional GE results. Accordingly, the observed steady-state mobilities from EMOFPAP do have similar behavior with those measured by conventional GE.

EXAMPLE 6

Figure 5:
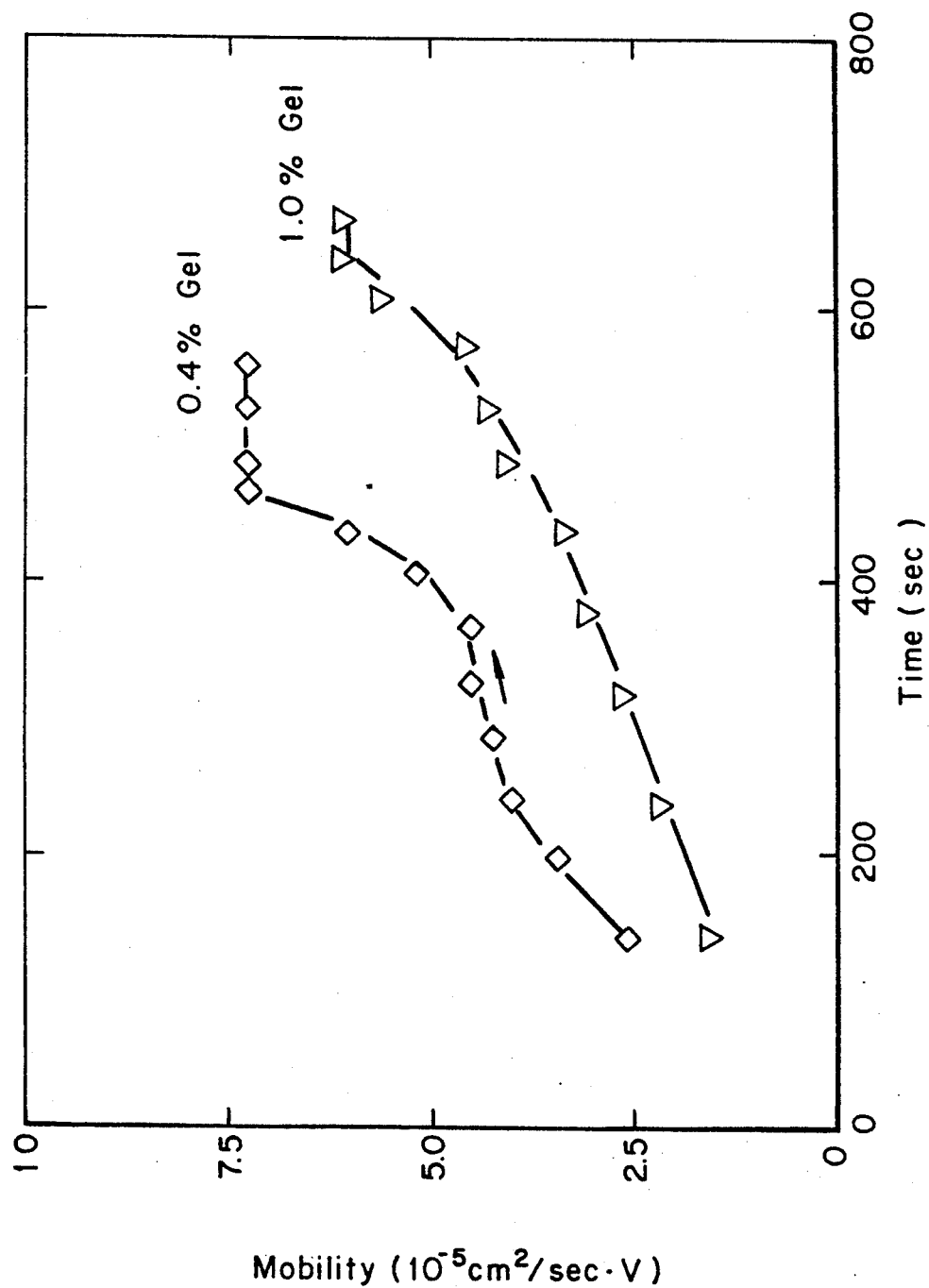
FIG. 5 is a graph showing the time-dependent mobility profile for λ DNA-EB in 0.4% and 1% agarose gels at E=3.5 V/cm, as described in Example 6.

Time-dependent mobility profile for λ DNA in 0.4% and 1.0% agarose gels at E=3.5 V/cm was determined. FIG. 5 shows the effect of different gel concentrations on the time-dependent mobility of λ DNA at a constant voltage, E=3.5 V/cm. Interestingly, there is a transition in the shape of the time-dependent mobility over gel concentrations that have been measured, as can be clearly seen in FIGS. 4 at graph (a) and 5.

By calculating the DNA size based on the worm-like chain model and estimating the gel pore size according to the equations provided by various investigators, Slater et al., *Biopolymers*, 27, 509 (1988); Reghetti et al., *Biochem. Biophys. Methods*, 4, 347 (1981); Stellwagen, *Biopolymers*, 24, 2243 (1985); Serwer and Allen, *Electrophoresis*, 4, 273 (1983); and Serwer and Hays *Anal. Chem.*, 158, 72 (1986), it has been found that the average ratios γ of DNA size (radius gyration) to gel pore size (pore radius) are ~2 for N4 DNA in 0.2% gel, ~3 for λ DNA in 0.4% gel, and ~6 for λ DNA in 1.0% gel. If the time-dependent mobility curve of λ DNA in 0.4% gel is divided into two parts and its inflection point as indicated by an arrow in FIG. 5, shows that the shape of the first part related to the initial field-on time is similar to that of N4 DNA at a more dilute gel concentration of 0.2% gel, while the shape of the second part of the later field-on time resembles that of λ DNA at a higher gel concentration of 1.0%. The observed shape transition on the time-dependent mobility might represent a transition in dominant deformation mechanisms of DNA when the gel pore size becomes comparable to the DNA size.

EXAMPLE 7

Figure 6A:
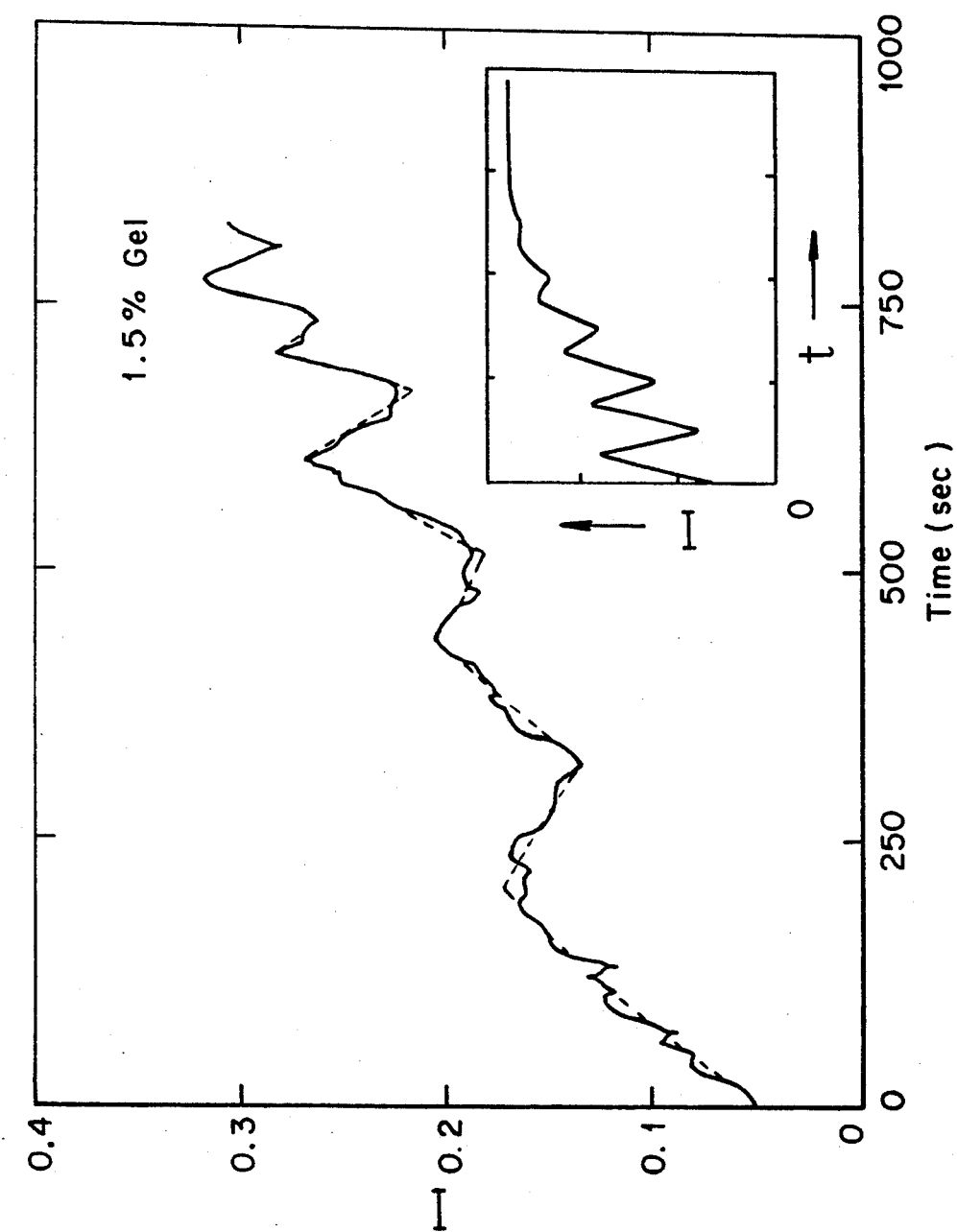
FIG. 6 (a) shows the fluorescence intensity trace vs. the electric-field-on time for λ DNA-EB in 1.5% agarose gel at E=3.5 V/cm, as described in Example 7. The dotted line denotes the assumed intensity trace from continuous movement of the bleached pattern. The insert shows the theoretical intensity trace when the bleached pattern moves continuously in uniformly.
Figure 6B:
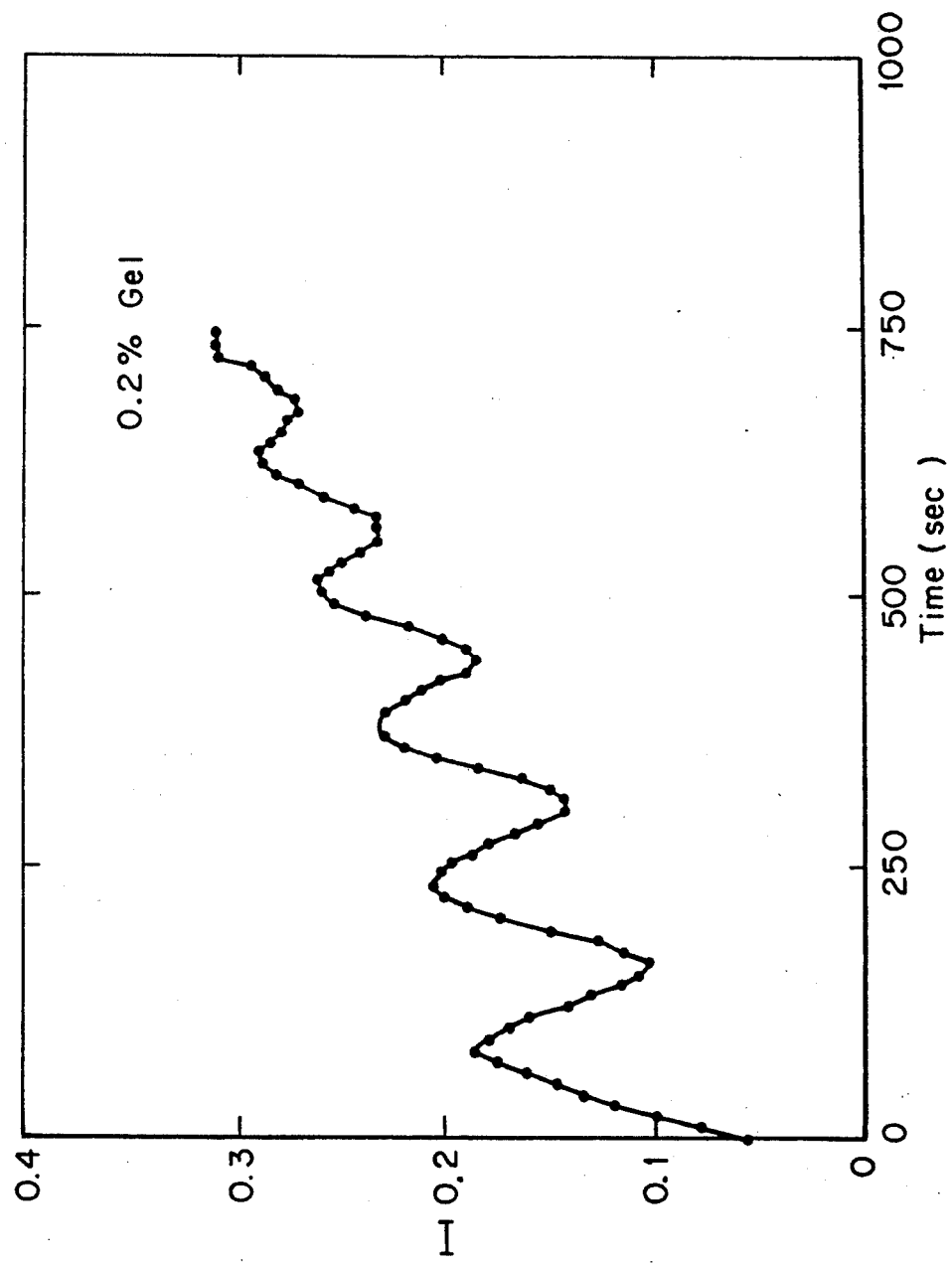

In this example florescence intensity vs. field-on time for λ DNA was measured in 1.5% agarose gel at E=3.5 V/cm and in 0.2% agarose gels at E=2.9 V/cm. Generally, PFGE is used in the γ region where the DNA size is much larger than the gel pore size. FIG. 6 at graph (a) shows a typical florescence intensity trace for λ DNA in 1.5% agarose gel at E=3.5 V/cm. Theoretically, when the photobleached periodic pattern moves continuously and uniformly, the sinasoidal intensity trace should follow a smooth upward trend as shown in the inset of FIG. 6 at graph (a). However, it is not difficult to see that there is a fluctuating fine structure superimposed on the oscillating intensity trace at the initial stage of FIG. 6 at graph (a). Since the intensity trace directly reflects the pattern movement (in the absence of diffusion), the fluctuations indicate the presence of localized motions that cannot be averaged out statistically even by the macroscopic periodic pattern consisting of millions of DNA molecules. Under these conditions, it was observed that there was ~10 seconds initial delay for the DNA molecules to start their movement after the electric field was applied. Then, the molecules moved faster (in the average time-dependent $\mu$) for some time, over an average period of 10-20 sec, and slower for some other time over comparable time periods. The faster-slower fluctuations lasted for about 600 sec and died out finally when $\mu$ reached its steady-state value.

FIG. 6 at graph (b) shows the florescence intensity trace for electric-field on time for λ DNA in 0.2% agarose gel at E=2.9 V/cm. The fluctuations were also observed at other high-level concentrations, e.g. 1.0% but not at lower gel concentration, e.g. 0.2% as shown in FIG. 6 at graph (b). The fluctuation times and their presence varied with the experimental conditions, such as gel concentration and field strength. So, the deformation of DNA molecules in small gel pores under an applied electric field is not just a simple stretching process.

Deutsch, in *Science*, 240, 922 (1988), *J. Chem. Phys.*, 90, 7436 (1989); and Deutsch et al., and *J. Chem. Phys.*, 90, 2476 (1989) pointed out that the chain motion differed from the standard reptation on a microscopic scale because of limited internal degrees of freedom for the DNA chain. In this example, the monitored time scale went down to a few seconds. The observed fluctuating fine structure in the florescence intensity signal could suggest a more detailed model for a short-time-averaged electrophoretic motion and deformation for large DNA in gels. The DNA chains stretch out and move under an external electric force. During the forward migration along the field direction, the chains could be hooked by the obstacles of the gel network due to some intermolecular and intramolecular interactions, and then the movement slows down or stops. The cycle grows with increasing field-on time and the chains reach different extents of elongation. The result of the competition between the active external electric force and the passive frictional force is a net movement. Finally, the deformation of chains reaches some equilibrium state and the molecules migrate in a gel network uniformly. The observation made in these examples is very similar to the oscillation between stretched and collapsed chains proposed by Deutsch. A mathematical analysis and model of the results of this example has been presented by Wu, Wang and Chu, in *Biopolymers*, 29, 491-500 (1990) and is discussed in Appendix A.

Thus, while the presently contemplated preferred embodiments of the present invention have been described, further changes and modifications could be made by those skilled in the art without departing from the spirit and scope of the invention. It is contemplated to claim all such changes and modifications.

APPENDIX A

The Results of Example 7

Ideally, when a Ronchi ruling is used as a photobleaching mask to generate periodic writing ($I_w$) and reading ($I_r$) beams, both $I_w$ and $I_r$ should be step functions and have the following forms:

$$I_w(x) = I_{i,w} f(x) \qquad (4)$$

and $$I_r(x) = I_{i,r} f(x) \qquad (5)$$

where $I_{i,w}$ and $I_{i,r}$ are the initial intensity of $I_w$ and $I_r$, respectively, and F(x) is a unit-amplitude square wave (jumping between 1 and 0) with period L, which can be written using the Fourier series with $K = 2\pi \sin(\Theta)/L$ $$f(x) = \frac{1}{2} + \frac{2}{\pi} \sum_{n=1}^{\infty} \frac{\sin(2n-1)Kx}{2n-1} \qquad (6)$$

where $\Theta$ is the angle between the incident light beam and sample plane, which is usually set at 90°. The distribution of fluorescence in the specimen immediately after photobleaching can be described by the function $$C(x,O) = C_o - \gamma I_w(x) = C_o - \Delta C f(x) \qquad (7)$$

where $\gamma$ is a constant representing the bleached fluorescence concentration per unit incident laser light intensity. $C_o$ and $\Delta C (= \gamma I_{i,w}$ and $o \leq \Delta C \leq C_o)$ are the initial fluorescence concentration before photobleaching and the bleached fluorescence concentration, respectively.

If it is assumed that the particles making up this distribution diffuse randomly and that the rotational diffusion of the particles can be ignored, each spatial frequency component of C(x,O) decays exponentially and has a characteristic rate. At time t after photobleaching, C(x,t) can be expressed as $$C(x,t) = C_o - \Delta C g(x,t) \qquad (8)$$

with $$g(x,t) = \frac{1}{2} + \frac{2}{\pi} \sum_{n=1}^{\infty} \exp[-DK^2(2n-1)^2 t] \frac{\sin[(2n-1)Kx]}{2n-1} \qquad (9)$$

where D is the translational diffusion constant. In the presence of the electrophoresis process, the whole photobleached periodic pattern moves spatially on top of the diffusion process. By considering both processes, it can be written C(x,t) as $$C(x,t) = C_o - \Delta C g(x - vt, vt) \qquad (10)$$

with $$g(x - vt, vt) = \frac{1}{2} + \qquad (11)$$

$$\frac{2}{\pi} \sum_{n=1}^{\infty} \exp[-(D/v)K^2(2n-1)^2 vt] \frac{\sin[(2n-1)K(x-vt)]}{2n-1}$$

where v is the speed of the moving photobleached periodic pattern in the x direction, and can be related to the electrophoretic mobility ($\mu$) and the applied electric field (E) by $\mu = v/E$.

The detector photocurrent F(t) is proportional to the fluorescence emission per spatial period. For the moving fluorescence pattern, the intensity cannot be normalized intensity by L as described by Lanni and Ware, *Rev. Sci. Instr.*, 53, 905-908 (1982). Instead, an unnormalized form is used in order to compare Equation (12) with the experimental results obtained in Example 7, based on the present optical geometry. Accordingly, the detector photocurrent F(t) is represented by:

$$F(t) = \alpha \int_O^L I_r(x) C(x,t) dx = \qquad (12)$$

$$\frac{1}{2} \alpha L I_{i,r} \left( C_o - \frac{\Delta C}{2} \right) - \frac{2}{\pi^2} \alpha L I_{i,r} \Delta C \sum_{n=1}^{\infty} \frac{1}{(2n-1)^2}$$

$$\exp[-DK^2(2n-1)^2 t] \cos[(2n-1)Kvt]$$

where $\alpha$ is a proportional constant. Equation (12) has a dc component and a set of decaying AC components, each of which has its own characteristic decay constant $\{\tau_{2n-1} = 1/[DK^2(2n-1)^2]\}$ and modulation frequency ($f_{2n-1} = (2n-1) Kv/(2\pi)$). The cross terms between different spatial frequencies in the photobleached pattern [C(x,t)] and in the illumination pattern [$I_r(t)$] make no contribution to F(t) because they are orthogonal functions under spatial integration. The first few oscillating terms dominate contributions to F(t) because, in addition to the exponential damping term, the prefactor $[1/(2n-1)^2]$ inside the sum decreases very fast with increasing n. Experimentally, by measuring the basic oscillating frequency $[f_1=(Kv/2\pi)=v/L]$ in F(t), v can be calculated for a known fringe spacing L. Four calculated curves from Equation (12) using different ratios of D/v (ranging from 0.0001 to 0.01) are shown in FIG. 7, where L=0.25 and $\Delta C=C_o=1$, so that F(t) started at zero and the time t was rescaled to vt by simply multiplying t with v. In FIG. 7, it is noted that it is very difficult to obtain the electrophoretic mobility if D/v>0.01.

Unfortunately, the real experimental data are not expected to follow this idealized theory. The open triangles in FIG. 8 show the results obtained in Example 7.

Figure 8:
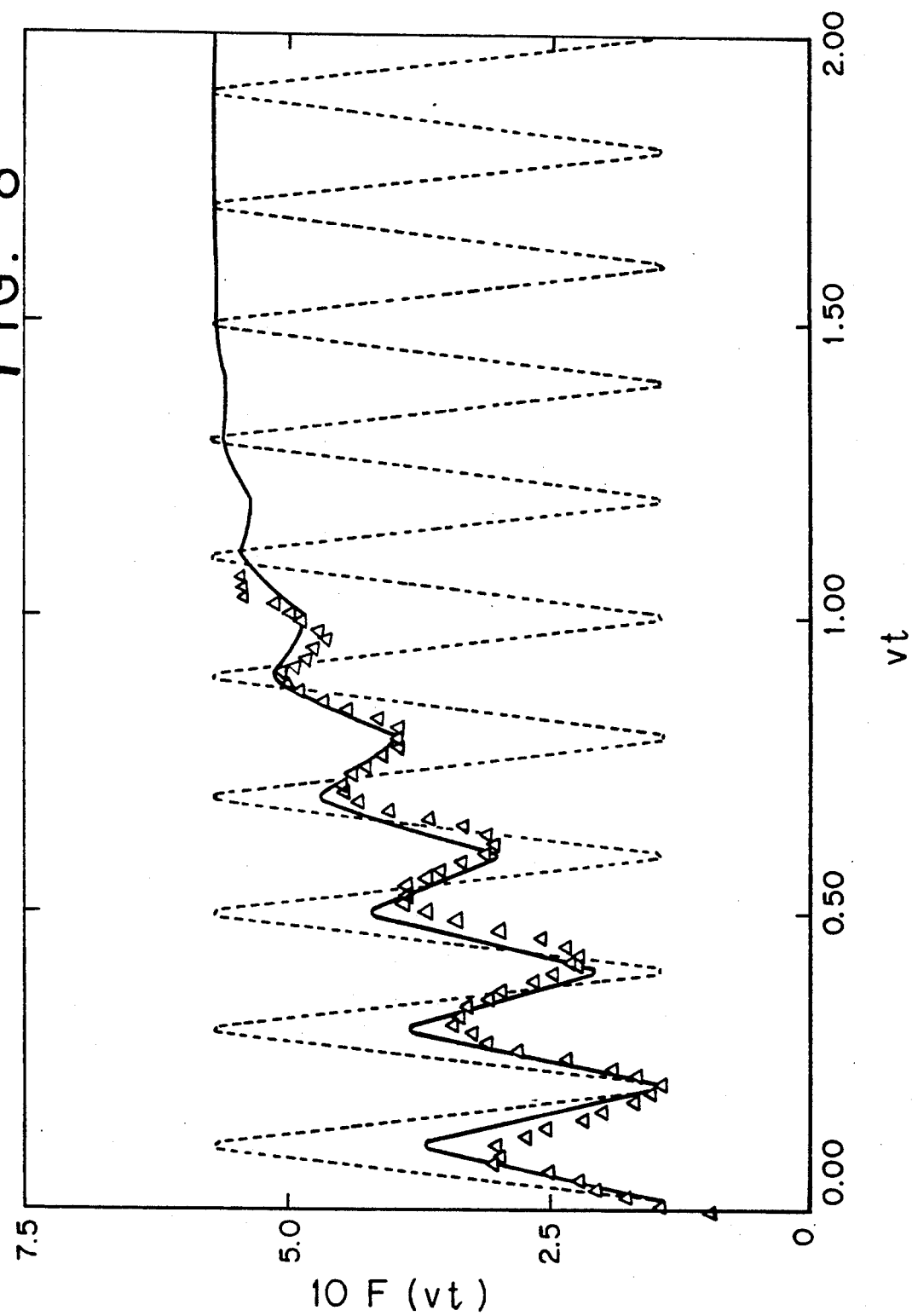
FIG. 8 is a graph comprising the calculated results from Equation (12) (dashed line) and Equation (26) (solid line) with real experimental data (hollow triangles) derived in Example 7 (FIG. 6 at graph (b)). The experimental conditions have been rescaled with $C_o=1$, $r=1$, $\Delta C=1$, $I_{o,r}=1$, $\alpha=1$, L=0.2, and D/v=0.

In FIG. 8, experimental conditions have been rescaled for comparison, i.e., r=1, $C_o=1$, L=0.2, and D/v=0, because the translational diffusion of large DNA fragments in agarose gels is much smaller than the electrophoretic mobility. For comparison, a calculated curve (dashed line) is also plotted in FIG. 8 by using Equation (12) with the same rescaled experimental conditions. The difference is so great that a further explanation must be found. In fact, the following conditions have not been taken into account in the idealized theory: (a) Both the illumination pattern and the photobleached pattern are not one-dimensional objects; (b) The laser beam intensity is not uniform spatially, but has a Gaussian profile; (c) Both the illumination pattern and the photobleached pattern have a finite size; and (d) Both $I_w$ and $I_r$ have constant background intensity $I_{B,w}$ and $I_{B,r}$, respectively, i.e., the illumination (or the photobleached) pattern does not have a perfect "bright" and "dark" periodic pattern. Therefore, for a more realistic comparison of EMOFPAP experimental data with theory, at least the above four conditions must be included in the theoretical consideration of the problem. In the following discussion some experimental optimization conditions for EMOFPAP are explored.

Figure 9:
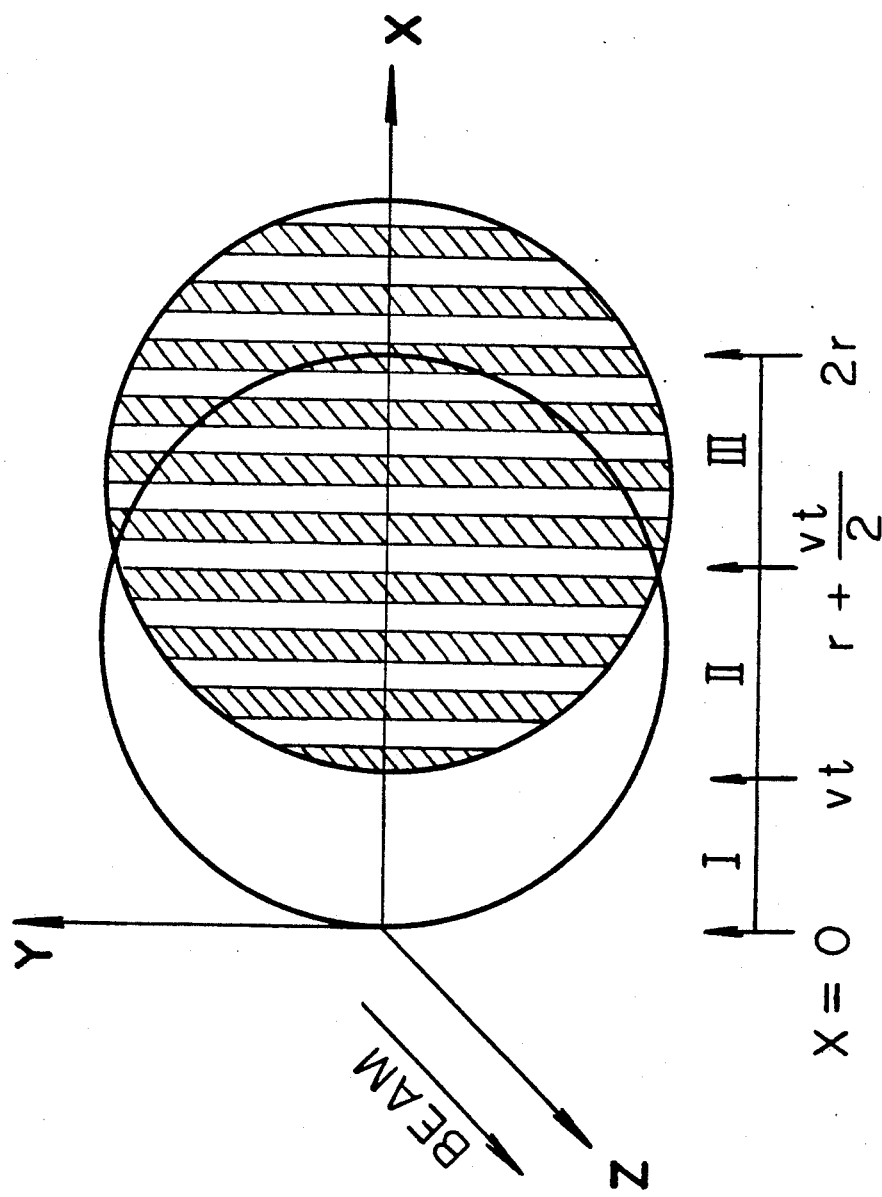
FIG. 9 is a schematic depiction for three parts of the integrations in Equation (18) for the bleached pattern at time t, where time has been rescaled with v.

If (1) both $I_w$ and $I_r$ beams are plotted along the z direction and the applied electric field is plotted in the x direction, and approximating (2) the cross section of the laser beam to be a perfect circle, the boundary of the circle with center located at (r,O) can be expressed as $y(x)=\pm[r^2-(r-x)^2]^{\frac{1}{2}}$, where r is the radius of the beam cross section and $0 \leq x \leq 2r$ (cf. FIG. 9). (3) The beam has a Gaussian profile, which can be written as $G(x)=\exp\{-[(x/r)-1]^2/(2\sigma^2)\}$ with the constant $\sigma^2$, defined by $\int(x-\bar{x})^2G(x)dx$. Based on the above conditions, the photobleaching and illumination patterns, $I_w$ and $I_r$, within the circle of $y(x)=[r^2-(r-x)^2]^{1/8}$, whose center is located at (r,O), can be written as $$I_w(x) = I_{B,w} + I_{0,w}f(x)G(x) \tag{13}$$

and $$I_r(x) = I_{B,r} + I_{0,r}f(x)G(x) \tag{14}$$

where $I_{B,w}+I_{O,w}=I_{i,w}$ and $I_{B,r}+I_{O,r}=I_{i,r}$. It should be noted that outside the circle, there is no laser light at all, i.e., $I_w(x>2r)=0$ and $I_r(x>2r)=0$. The ratios of $I_{O,r}/I_{B,r}$ and $I_{O,w}/I_{B,w}$ actually determine the contrast of the photobleaching and illumination beam patterns. Corresponding to the change in $I_w(x)$, C(x,O) should also consist of two parts. Within the illumination area, C(x,O) has the form $$\begin{aligned}C(x,O)&=C_o-\gamma[I_{B,w}+I_{o,w}f(x)G(x)]\\&=C_o-C_B-\Delta Cf(x)G(x)\end{aligned} \tag{15}$$

where $C_B(=\gamma I_{B,w})$ is the photobleached fluorescence concentration produced by the constant background in $I_w(x)$. Outside the illumination area, the fluorescence concentration remains at $C_o$. The ratio $\Delta C/C_B$ actually determines the extent of photobleaching. At time t, the whole photobleached pattern moves a distance of vt along the x direction. Within the circle, $y(x)=\{r_2-[r-(x-vt)]^2\}^{1/8}$, where the center of the circle has moved to x=r+vt, C(x,t) can be expressed as $$C(x-vt,vt)=C_o-C_B-\Delta Cg(x-vt,vt)G(x-vt)0\leq vt \leq 2r \tag{16}$$

while outside the circle, C(x,t) remains at $C_O$. The detector photocurrent now is the total fluorescence emission from the illumination area, i.e., $$F(t) = \alpha \int_O^{2r} C(x,t)I_r(x)y(x)dx \tag{17}$$

where the function y(x) is used for limiting the integration within the illumination area. In order to perform this integration, Equation (17) has to be divided into three parts, which are schematically shown in FIG. 9.

$$F(t) = \alpha \int_O^{vt} C(x,t)I_r(x)y(x)dx + \tag{18}$$

PART I $$\alpha \int_{vt}^{r+vt/2} C(x,t)I_r(x)y(x)dx + \alpha \int_{r+vt/2}^{2r} C(x,t)I_r(x)y(x)dx$$

PART II          PART III

For Part I, $C(x,t)=C_O$, it can be integrated and written as $$\text{PART I} = \alpha \int_O^{vt} C_o I_r(x)y(x)dx \tag{19}$$

For Part III, C(x,t)=C(x−vt,vt), it can also be integrated and written as $$\text{PART III} = \alpha \int_{r+vt/2}^{2r} C(x-vt,vt)I_r(x)y(x)dx = \tag{20}$$

$$\alpha \int_{r+vt/2}^{2r} [C_O - C_B - \Delta Cg(x-vt,vt)G(x-vt)]I_r(x)y(x)dx$$

$$\times G(x-vt)]I_r(x)y(x)dx \tag{21}$$

Figure 10:
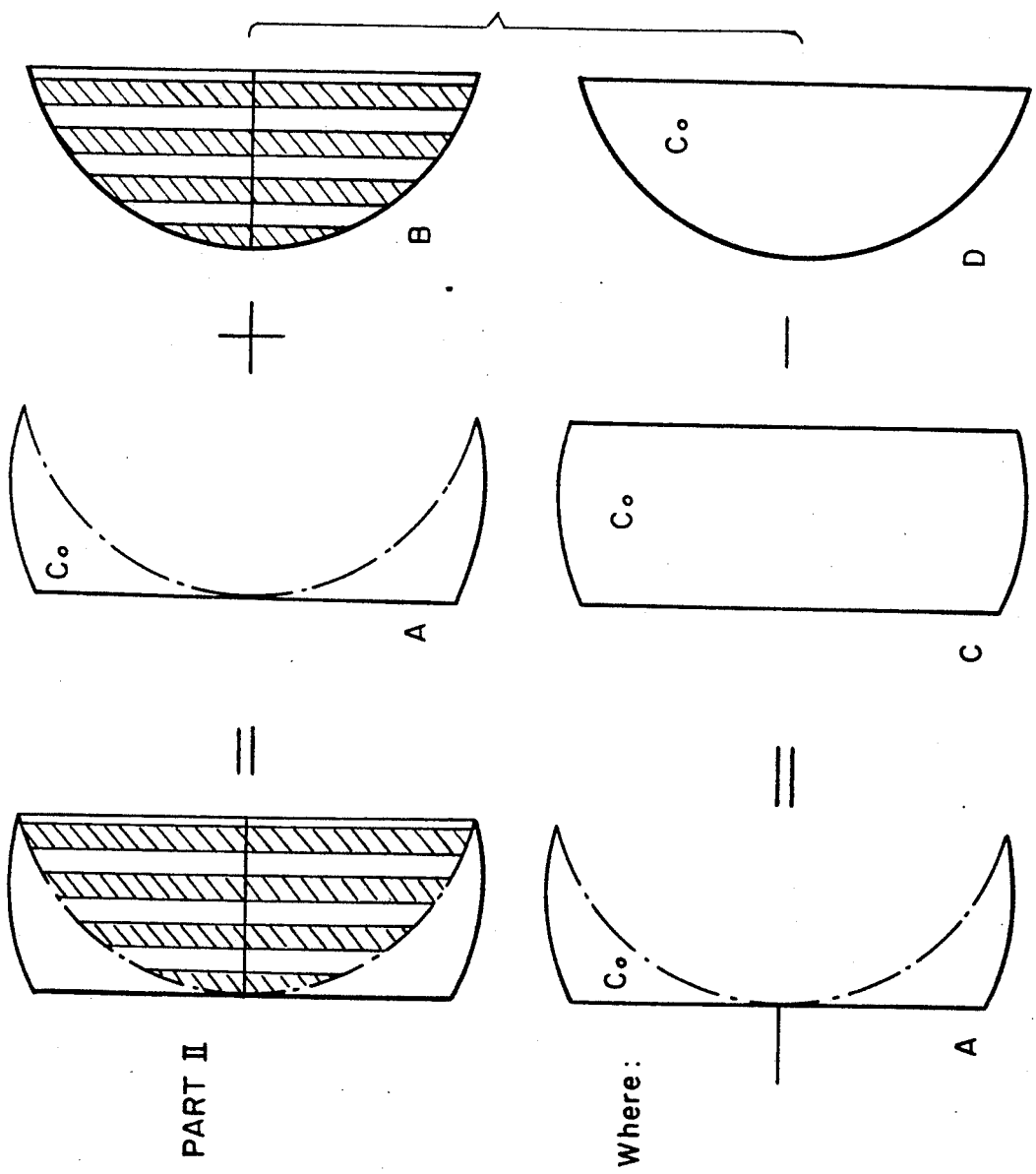
FIG. 10 is a the schematic depiction for the integration of Part II in Equation (18).

The only difficult one is Part II. After carefully examining the Part II in FIG. 10, it was found that Part II can be considered as a combination of another three small parts and graphically expressed in FIG. 10. It is clear that

PART II = A + B = C − D + B  (22)

because $A = C - D$. Inside area C and D, $C(x,t) = C_O$
The integration of C and D can be written as follows:

$$\text{PART C} = a \int_{vt}^{r+vt/2} C_O I_r(x) y(x) dx \quad (23)$$

and, $$\text{PART D} = a \int_{vt}^{r+vt/2} C_O I_r(x) y(x - vt) dx \quad (24)$$

where $y(x)$ has been replaced by $y(x-vt)$ because the integration is bounded by the circle of bleached pattern instead of the circle of illumination pattern. Similarly, Part B should be integrated as $$\text{PART B} = a \int_{vt}^{r+vt/2} C(x - vt, vt) I_r(x) y(x - vt) dx \quad (25)$$

because $C(x,t) = C(x-vt,vt)$ inside area B. Combining Equations (18)-(25), F(t) can now be written as $$F(t) = a \int_0^{2r} C_O I_r(x) y(x) dx - \quad (26)$$

$$a \int_{r+vt/2}^{2r} [C_B + \Delta C g(x - vt, vt) G(x - vt)] I_r(x) y(x) dx -$$

$$-a \int_{vt}^{r+vt/2} [C_B + \Delta C g(x - vt, vt) G(x - vt)] I_r(x) y(x - vt) dx$$

Figure 11:
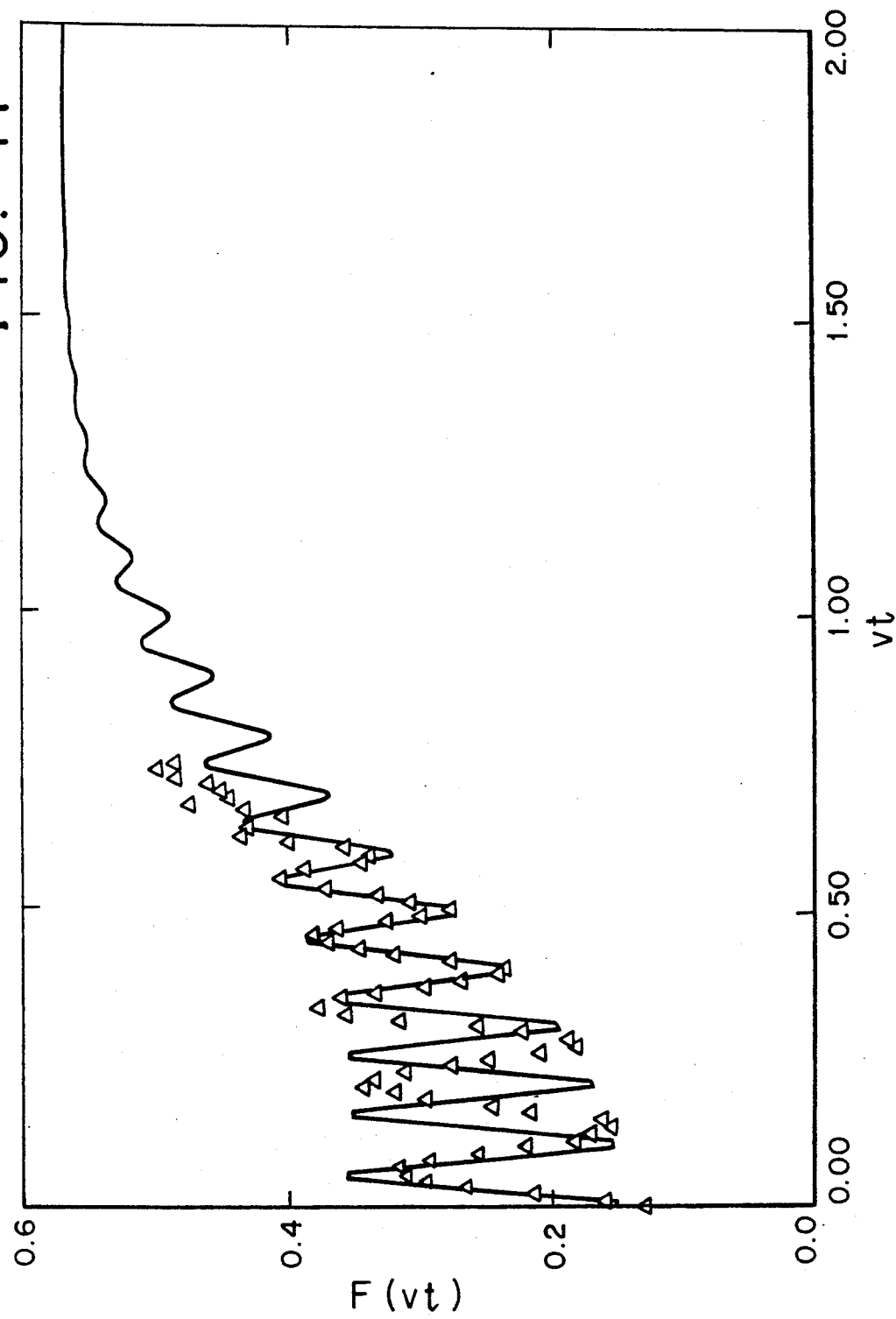
FIG. 11 is a graph showing a comparison of calculated results from Equation (26) (solid line) with real experimental data (hollow triangles) derived in Example 7 (FIG. 6 at graph (b)). The experimental conditions have been rescaled with $C_o=1$, $r=1$, $\Delta C=1$, $I_{o,r}=1$, $\alpha=1$, L=0.1, and D/v=0. The stationary mobility $\mu$ is $4.54\times 10^{-5}$ cm²/s−V.
Figure 12:
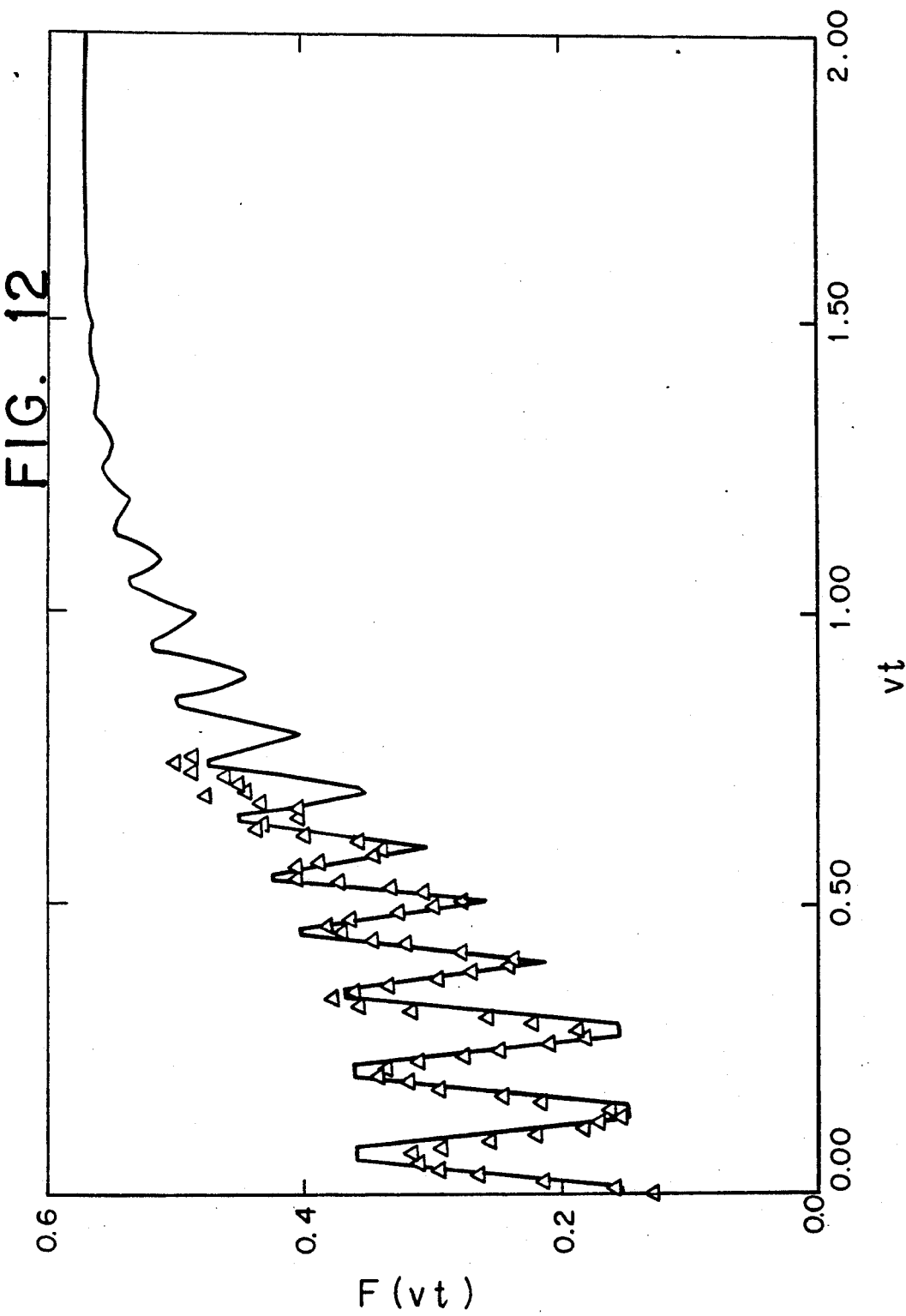
FIG. 12 is a graph showing the calculated results from Equation (26) (solid line) with real experimental data (hollow triangles) derived in Example 7 (FIG. 6 at graph (b)). The experimental conditions have been rescaled with $C_o=1$, $r=1$, $\Delta C=1$, $I_{o,r}=1$, $\alpha=1$, L=0.1, and D/v=0. The two stationary mobilities, $\mu_{low}=3.02\times 10^{-5}$ cm²/s−V and $\mu_{high}=4.54\times 10^{-5}$ cm²/s−V, have been chosen to fit the experimental data.

The solid line in FIG. 8 expresses a calculated result from Equation (26) for the same rescaled experimental conditions. The agreement and fit between the calculated curve and experimental data is very good. It is also apparent that the modulated frequencies for the real experimental data during the initial stages are different from those at the later stages. The modulated frequencies for the real experiment (Example 7) gradually approach a constant value. The difference between the real experimental data and the calculated data using a constant electrophoretic mobility is understandable because there is a stretching process mixed with the electrophoresis process during the initial application of the external electric field. This difference is more clearly shown in FIG. 11 where the spacing has been doubled by changing the frequency of the Ronchi ruling from 100 lines/inch to 200 lines/inch. Note that in FIG. 11, the electrophoretic mobility is slower at the initial stage. It shows that one single constant frequency [i.e., v because $\omega = (2\pi/L)v$] in Equation (26) cannot quite fit the real experimental data. A time-dependent electrophoretic mobility $\mu(t)$, therefore, had to be introduced. FIG. 12 shows the results when $\mu_{low}( = 3.02 \times 10^{-5} cm^2/s - V)$ was chosen for the initial stage mobility and $\mu_{high}$ ($=4.54 \times 10^{-5}$ s−V) was chosen for the later stage mobility. The fit is fairly good as shown by FIG. 12. Note that $\mu(t)$ will depend on many factors, including the agarose gel concentration, the "mesh size distribution" of the agarose gel, and the size of DNA fragments. It is also interesting to note that the fluorescence signal is smeared after about seven periods, probably because of the spatial inhomogeneities in the agarose gel and the small signal-to-noise ratio due to the decrease of overlap between the illumination pattern and the photobleached pattern. The measured change in mobility together with the degree of stretching should help in the investigation of the dynamics of DNA in agarose gels in the presence of the applied pulsed electric field on a more microscopic scale.

By utilizing Equation (26), F(t) can be computed using a set of different experimental conditions. For simplicity, let $C_O = 1$, $r = 1$, $a = 1$, and $L = 0.25$. In order to determine how the self-translational diffusion of the particles of interest affects EMOFPAP, a set of calculated curves with different values of D/v are plotted in FIG. 13. It has been determined that it is very difficult to perform the EMOFPAP experiment when D/v is larger than $\sim 10^{-3}$, which is one order smaller than the value ($\sim 10^{-2}$) predicted by idealized theory in FIG. 7. In practice, it shows that the larger the particle of interest and the more concentrated the gel, the easier the EMOFPAP can be performed. For a given size particle, the requirement of the D/v ratio is satisfied either by increasing the gel concentration in order to reduce D or by increasing the electric field in order to increase v. In further considering how the contrasts of the photobleaching ($I_w$) and illumination ($I_r$) patterns affect the performance of the EMOFPAP, FIG. 14 shows three calculated F(vt) vs. vt curves. It shows that the sharper the contrast of the pattern, the better the signal-to-noise ratio. Experimentally, a perfect bright and dark periodic pattern is never achieved because of the recombination of the diffraction pattern from the Ronchi ruling by a finite size lens, scattering from the glass walls of the sample cell, and even the sample itself.

Figure 13:
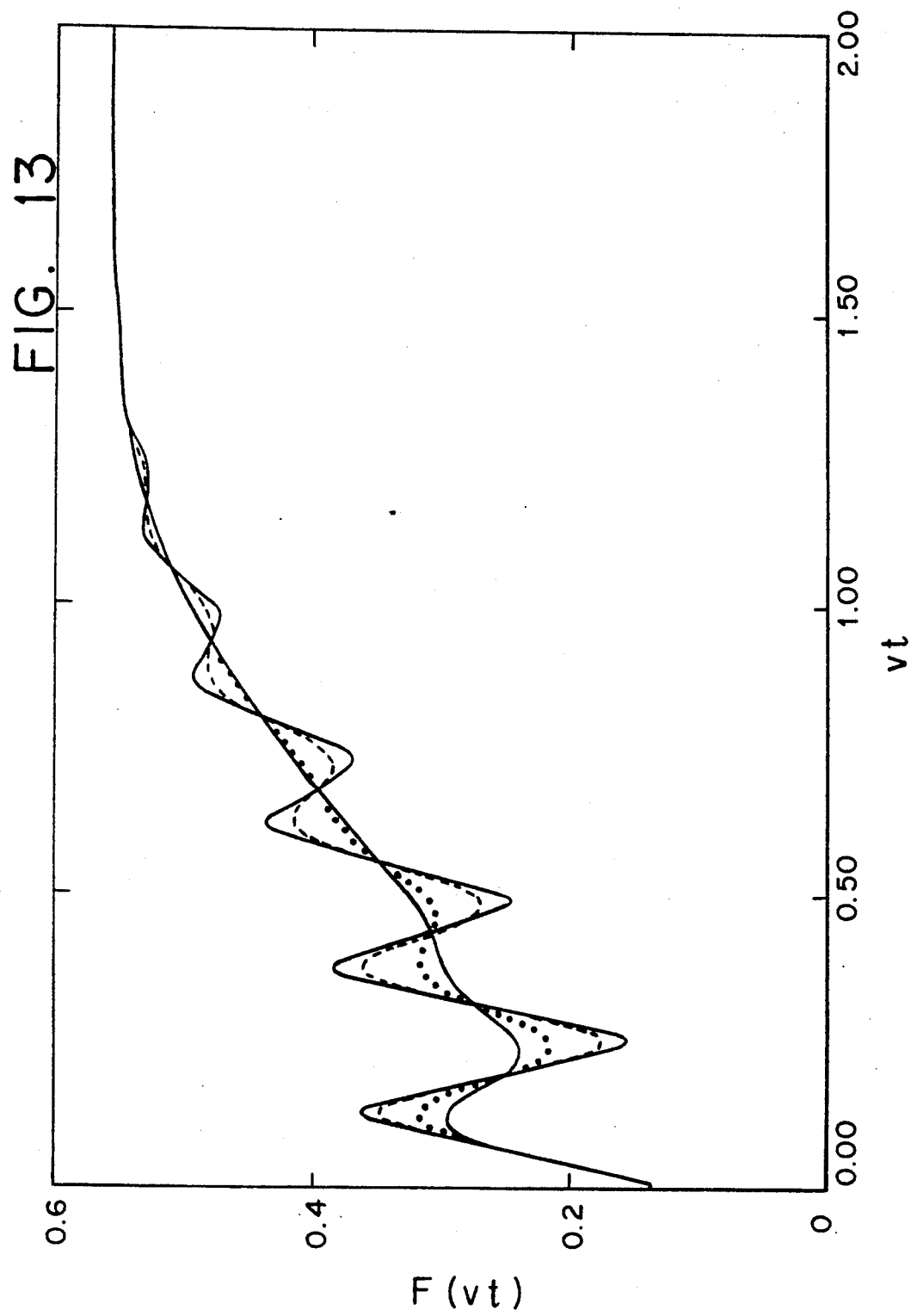
FIG. 13 is a graph showing the calculated values of F(vt) vs. vt at different values of D/v by using Equation (26), where $I_{B,r}=0.2$, $I_{o,r}=0.8$, $C_B=0.25$, and C=0.75. The remaining conditions and the line styles are the same as in FIG. 8.
Figure 14:
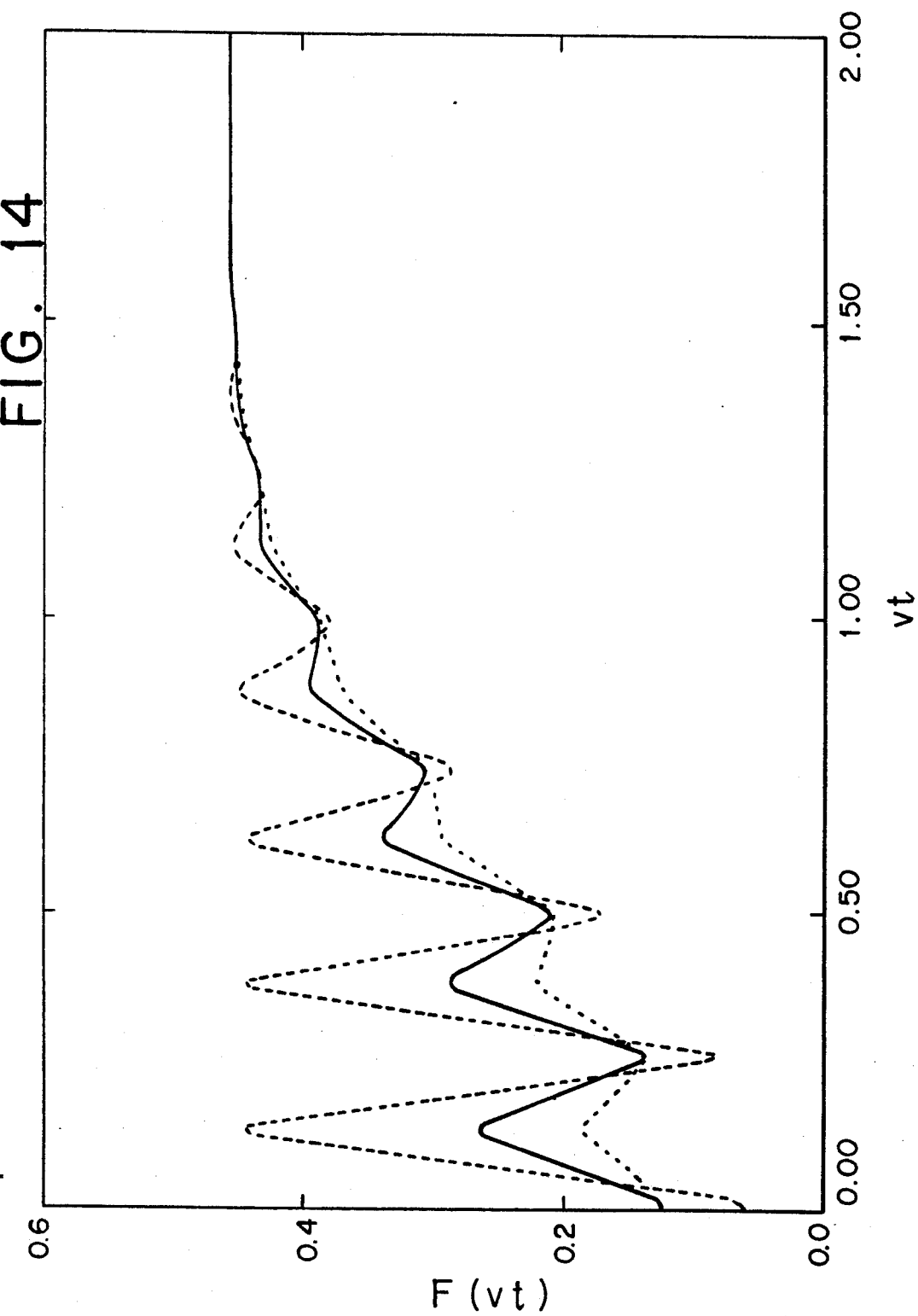
FIG. 14 is a graph showing the calculated values of F(vt) vs. vt by using Equation (26) with $C_o=1$, $r=1$, $\alpha=1$, L=0.25 and $D/v=10^{-4}$, but different values of $I_{B,r}$, $I_{o,r}$, $C_B$ and $\Delta C$. The dashed line for $I_{B,r}=0$, $I_{o,r}=1$, $C_B=0$ and C=1 shows a sharp bleached and illumination pattern. The solid line for $I_{B,r}=0.3$, $I_{o,r}=0.7$, $C_B=0.3$ and $\Delta=C=0.7$ shows a more realistic pattern. The dotted line for $I_{B,r}=0.5$, $I_{o,r}=0.5$, $C_B=0.5$ and $\Delta C=0.5$ shows a poor contrast, which limits the experimental measurement.

FIG. 13 also shows that the condition $I_{O,r} >> I_{B,r}$, is an essential condition. In order to improve the experimental conditions, a large diameter and high-quality lens should be used in order to recombine the diffraction pattern from the Ronchi ruling, put the sample exactly at the image point of the Ronchi ruling, and make the cell surface as clean as possible. Physically, it is now known that the extent of photobleaching will effect the signal-to-noise ratio.

Figure 15:
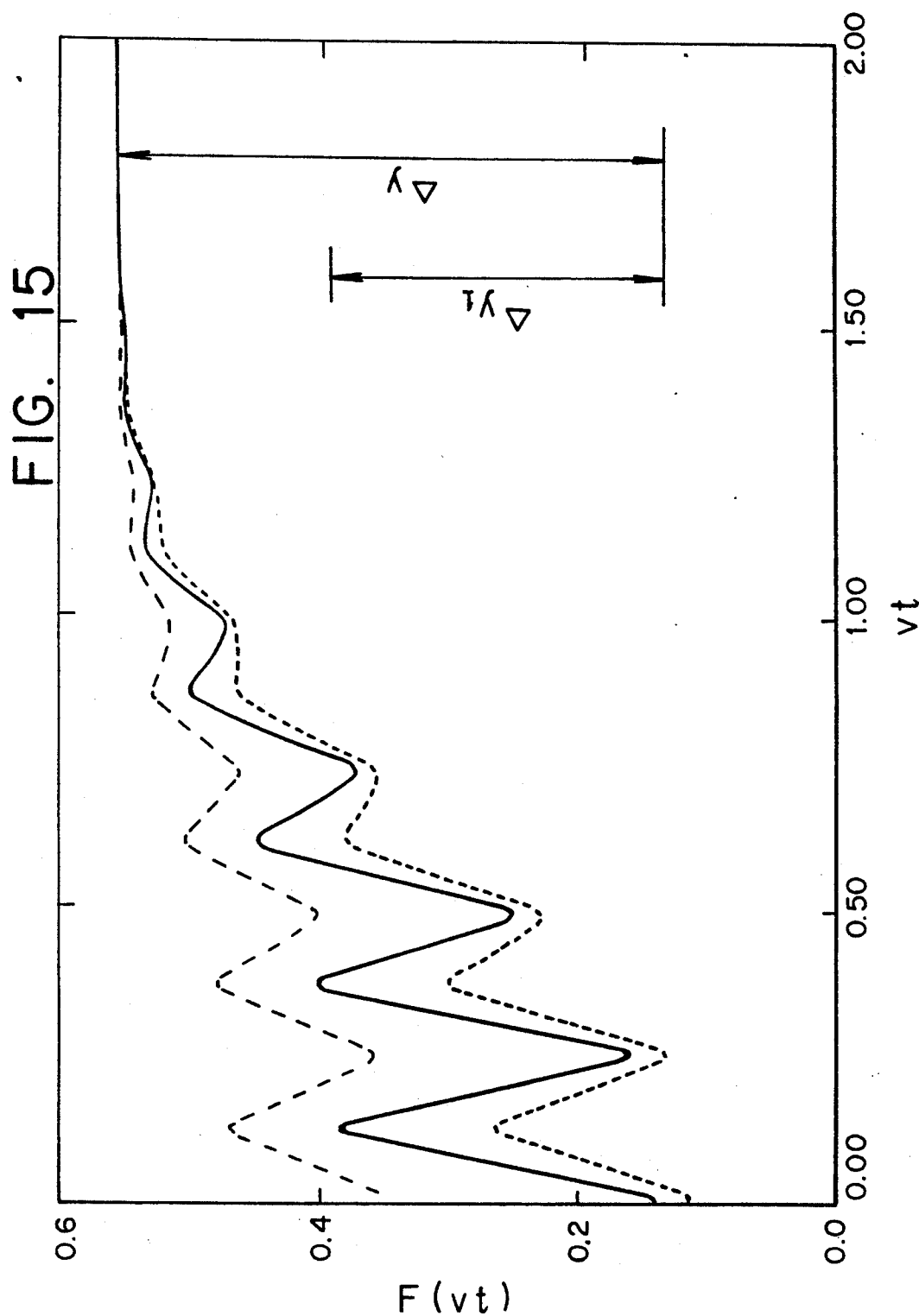
FIG. 15 is a graph showing the calculated values of F(vt) vs. vt by using Equation (26) with $C_o=1$, $r=1$, $I_{B,r}=0.2$, $I_{o,r}=0.8$, $\alpha=1$, L=0.25 and $D/v=10^{-4}$, but different values of $C_B$ and $\Delta C$. The dashed line for $C_B=0.5$ and C=0.5 shows an overbleached case. The dotted line for $C_B=0.1$ and C=0.4 shows an incompletely bleached case. The solid line for $C_B=0.2$ and $\Delta C=0.8$ shows a completely bleached case.

FIG. 15 shows three calculated F(vt) vs. vt curves at a different extent of photobleaching. From FIG. 14, it is found that there is an optimization point about the bleaching extent where the bright part of the bleaching pattern ($I_w$) just bleaches out all fluorescence molecules within the pattern. This condition has to be determined experimentally because it involves many experimental conditions, such as laser light intensity, thickness of the sample, photon quantum efficiency, type of fluorescence molecules, etc. With $I_{laser} = 400$ mW, the signal-to-noise ratio was measured after different bleaching times. The results are listed in Table I where $\Delta y$ and $\Delta y_1$ have been defined schematically in FIG. 15. The optimized photobleaching time is around 50 s.

TABLE 1

| Fluorescence Recovery Intensity After Different Bleaching Times | | | |
|---|---|---|---|
| Bleaching time (sec) | $\Delta y(V)$ | $\Delta y_1$ | $\Delta y_1/\Delta y(\%)$ |
| 15 | 0.25 | 0.41 | 56 |
| 40 | 0.51 | 0.29 | 57 |
| 50 | 0.67 | 0.38 | 56 |
| 60 | 0.74 | 0.35 | 47 |

Finally, the method of using two coherent crossing laser beams to produce an interference pattern that serves as the photobleaching and the illumination periodic patterns is analyzed. Both the photobleaching and the illumination patterns formed in this manner have the sine-function form. By simply changing f(x) in Equation (26) from a step function to a sine function, F(vt) vs. vt can be calculated by crossing two coherent laser beams to form the photobleaching and the illumination periodic patterns. The dashed line in FIG. 16 shows the calculated F(vt) vs. vt by crossing two laser beams.

For the sake of comparison, a calculated F(vt) vs. vt curve is also plotted by using the Ronchi ruling as a mask (denoted by the solid line) using exactly the same condition. The crossed beam method gives a poorer signal-to-noise ratio because the sine function is more like a "smeared" step function, i.e., having less contrast. From this analysis, it is now understood known that the lower the contrast, the poorer signal-to-noise ratio. Experimentally, the method of crossing two coherent laser beams to produce the photobleaching and the illumination periodic patterns also requires more time for instrument alignment. The advantage of using two crossed laser beams, however, is the ability to achieve very small fringe spacings, L. Smaller fringe spacings, L, allow the separation time to be reduced, and possibly allows examination of more localized DNA movements if L is smaller than the contour length of DNA fragments. However, in most cases, using the Ronchi ruling or a mask is better and easier for the EMOFPAP method of the present invention.

I claim:

1. A process for detecting the mobility of fluorescent labeled molecules in response to a force, comprising:
   (a) placing fluorescent labeled molecules in a fluid medium;
   (b) imposing a force on the labeled molecules causing the molecules to move in the fluid medium;
   (c) photobleaching said labeled molecules in the fluid medium, leaving a first geometrically defined region of said labeled molecules having a defined boundary which has not been photobleached;
   (d) exciting said first geometrically defined region of said labeled molecules in the fluid medium with a reading beam having a second geometrically defined configuration of light and dark; and
   (e) detecting the intensity produced by the interaction of said reading beam configuration and the movement of said defined boundary of the first geometrically defined region of labeled molecules.

2. The process recited in claim 1, wherein said fluorescent labeled molecules are placed in a sample cell containing a substrate for electrophoresis.

3. The process recited in claim 2, wherein said substrate for electrophoresis is a gel.

4. The process recited in claim 2, wherein said sample cell is a capillary.

5. The process recited in claim wherein said force is an electrical potential difference imposed for electrophoretic separation of said fluorescent labeled molecules.

6. The process recited in claim 1, wherein said photobleaching and said reading beam are accomplished by an intense light source focused through a diffraction grating which produces a pattern of light and dark.

7. The process recited in claim 1, wherein said photobleaching and said reading beam, are accomplished by crossing of two beams from an intense light source to form an interference pattern.

8. The process recited in claim 1, wherein said photobleaching and said reading beam are accomplished by a beam from an intense light source focused through a mask.

9. The process recited in claim 1, wherein the intensity produced by the interaction of the reading beam configuration and the movement of said first geometrically defined region of labeled molecules is detected by using a photo detector.

10. The process of claim 1, further comprising modulating said reading beam having said second geometrically defined configuration as a function of the velocity of said labeled molecules through said fluid medium, whereby more than one species of said labeled molecules is detected.

11. The process recited in claim 1, wherein said labeled molecules comprise labeled particles.

12. An apparatus for detecting the mobility of fluorescent labeled molecules in response to a force, comprising:
   (a) means for retaining fluorescent labeled molecules in a fluid medium;
   (b) means for applying a force on the labeled molecules causing the molecules to move in the fluid medium within said retaining means;
   (c) means for photobleaching said labeled molecules in the fluid medium, leaving a first geometrically defined region of said labeled molecules which has not been photobleached wherein said means for photobleaching is a non-laser light source;
   (d) means for generating a reading beam which excites said first geometrically defined region of said labeled molecules in the fluid medium, said reading beam having a second geometrically defined configuration of light and dark; and
   (e) means for detecting the intensity produced by the interaction of the second geometrically defined configuration of said reading beam and the movement of said first geometrically defined region of labeled molecules.

13. The apparatus recited in claim 12, further comprising a sample cell containing a substrate for electrophoresis and for retaining said fluorescent labeled molecules.

14. The apparatus recited in claim 13, wherein said substrate for electrophoresis is a gel.

15. The apparatus recited in claim 13, wherein said sample cell is a capillary.

16. The apparatus recited in claim 12, wherein said means for applying a force further includes means for applying an electrical potential difference for separating said fluorescent molecules by electrophoresis.

17. The apparatus recited in claim 12, wherein said photobleaching and said reading beam are generated by means for focusing said non-laser light source through a diffraction grating producing a pattern of light and dark.

18. The apparatus recited in claim 12, wherein said photobleaching and said reading beam are generated by means for crossing of two non-laser light beams to form a interference pattern.

19. The apparatus recited in claim 12, wherein said photobleaching and said reading beam are generated by means for focusing a beam through a mask.

20. The apparatus recited in claim 12, wherein the intensity produced by the interaction of the reading beam configuration and the movement of said first geometrically defined region of labeled molecules is detected by a photo detector.

21. The apparatus of claim 12, further comprising means for modulating said reading beam having said second geometrically defined configuration as a function of the velocity of said labeled molecules through said fluid medium, whereby more than one species of said labeled molecules is detected.

22. The apparatus recited in claim 12, wherein said apparatus further comprises means for detecting the movement of fluorescent labeled particles in response to said force.

* * * * *